United States Patent
Yoon et al.

[11] Patent Number: 5,932,742
[45] Date of Patent: Aug. 3, 1999

[54] ARYLSULFONYLIMIDAZOLONE DERIVATIVES AS AN ANTITUMOR AGENT

[75] Inventors: Sung June Yoon, Seoul; Yong Ho Chung, Kyunggi-do; Moon Sun Lee, Kyunggi-do; Dong Rack Choi, Kyunggi-do; Jung A Lee, Seoul; Hee Soon Lee, Daejeon; Hae Ran Yun, Kyunggi-do; Dug Keun Lee, Kyunggi-do; Eun Yi Moon, Kyunggi-do; Hyun Sook Hwang; Chung Ha Choi, both of Seoul; Sang Hun Jung, Daejeon, all of Rep. of Korea

[73] Assignee: Dong Wha Pharm. Ind. Co., Ltd., Seoul, Rep. of Korea

[21] Appl. No.: 09/212,396

[22] Filed: Dec. 16, 1998

Related U.S. Application Data

[62] Division of application No. 08/915,726, Aug. 21, 1997.

[30] Foreign Application Priority Data

Aug. 22, 1996 [KR] Rep. of Korea ....................... 96-34920
Nov. 5, 1996 [KR] Rep. of Korea ....................... 96-51939
Nov. 12, 1996 [KR] Rep. of Korea ....................... 96-53450
May 19, 1997 [KR] Rep. of Korea ....................... 97-19365

[51] Int. Cl.$^6$ ................................................. C07D 403/12
[52] U.S. Cl. ........................................................ 548/312.1
[58] Field of Search ........................................... 548/312.1

[56] References Cited

U.S. PATENT DOCUMENTS

| | | |
|---|---|---|
| 4,845,128 | 7/1989 | Harper et al. . |
| 5,110,830 | 5/1992 | Harper et al. . |
| 5,116,874 | 5/1992 | Poore . |
| 5,169,860 | 12/1992 | Mohamadi et al. . |
| 5,254,582 | 10/1993 | Boder et al. . |
| 5,270,329 | 12/1993 | Scott . |
| 5,302,724 | 4/1994 | Howbert et al. . |
| 5,565,494 | 10/1996 | Grindey et al. . |
| 5,594,028 | 1/1997 | Harper et al. . |

FOREIGN PATENT DOCUMENTS 0 614 887  9/1994  European Pat. Off. .

OTHER PUBLICATIONS

Ji–Wang Chern et al, Journal of Medicinal Chemistry, vol. 40, No. 14, pp. 2276–2286, 1997, "Synthesis and Cytotoxic Evaluation of Substituted Sulfonyl–N–Hydroxyguanidine Derivatives as Potential Antitumor Agents".

Peter J. Houghton et al, Cancer Chemother Pharmacol, vol. 25, pp. 84–88, 1989, "Evaluation of N–(5–Indanylsulfonyl)–N$^1$–(4–Chlorophenyl)–Urea Against Xenografts of Pediatric Rhabdomyosarcoma".

J. Jeffry Howbert et al, Journal of Medicinal Chemistry, vol. 33, No. 9, pp. 2393–2407, 1990, "Novel Agents Effective Against Solid Tumors: The Diarylsulfonylureas. Synthesis, Activities, and Analysis of Quantitative Structure–Activity Relationships".

John E. Toth, et al, Journal of Medicinal Chemistry, vol. 40, No. 6, pp. 1018–1025, "Sulfonimidamide Analogs of Oncolytic Sulfonylureas".

*Primary Examiner*—Patricia L. Morris
*Attorney, Agent, or Firm*—Oblon, Spivak, McClelland, Maier & Neustadt, P.C.

[57] ABSTRACT

The present invention relates to a novel arylsulfonylimidazolone derivative represented by the following formula (I) which shows a superior antineoplastic activity in contrast to the known sulfonylurea antitumor agents as well as little side effect:

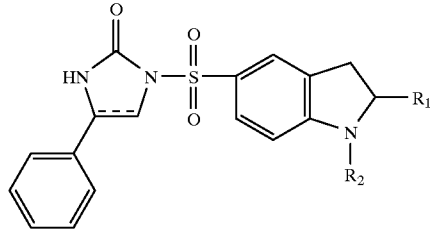

(I)

and its pharmaceutically acceptable salt and stereoisomer, in which - -, $R_1$, and $R_2$ are as defined in the specification.

2 Claims, No Drawings

ARYLSULFONYLIMIDAZOLONE DERIVATIVES AS AN ANTITUMOR AGENT

This application is a Division of application Ser. No. 08/915,726 filed on Aug. 21, 1997.

BACKGROUND of the INVENTION

1. Field of the Invention

The present invention relates to a novel arylsulfonylimidazolone derivative that exhibits potent antineoplastic activity. More specifically, the present invention relates to a novel arylsulfonylimidazolone derivative represented by the following formula (I) which shows a superior antineoplastic activity in contrast to the known sulfonylurea antitumor agents as well as little side effect:

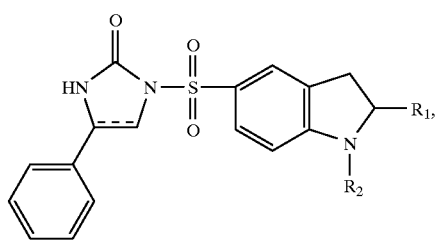

its pharmaceutically acceptable salt or stereoisomer, in which

= represents single or double bond, $R_1$ represents hydrogen or methyl, $R_2$ represents chloroacetyl; $C_1$–$C_5$alkylaminoacetyl; allylaminoacetyl; $C_1$–$C_4$ alkoxycarbonyl; nicotinyl; furanoyl; thiophenoyl; benzoyl which can be substituted by halogen, nitro, cyano, amino which can be substituted by nonpolar amino acid residue, hydroxy, methyl or methoxy which can be independently of one another substituted by halogen, ethoxy or chloroacetylamino; or

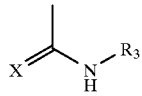

(wherein, X represents oxygen or sulfur atom, $R_3$ represents $C_1$–$C_4$alkyl, allyl, chloroacetyl or cyclohexyl, or phenyl which can be substituted by methoxy, fluoro, methyl, amino or methylthio).

The present invention also relates to a process for preparing the compound of formula (I), a novel intermediate which can be used for preparing the desired compound of formula (I), and an antitumor composition that includes the compound of formula (I) as an active ingredient.

2. Background Art

Many sulfonylureas that exhibit different kinds of activities from each other have been known in the art. Some of them have hypoglycemic activities, some of them have herbicidal activities, and some of them have antimycotic activities.

In recent years, it has also been reported in several literatures that certain diarylsulfonylureas have antineoplastic activity (see, U.S. Pat. No. 4,845,128(1989); European Patent Publication No. 0222475 (published on May 20, 1987); European Patent Publication No. 0291269 (published on Nov. 17, 1988); European Patent Publication No. 0467613 (published on Jan. 22, 1992); Grindey, et al., *American Association of Cancer Research,* 27:277 (1986); Houghton, et al., *Cancer Chemotherapy and Pharmacology,* 25:84–88 (1989)).

Sulofenur[N-(indan-5-sulfonyl)-N-(4-chlorophenyl)urea; LY186641] represented by the following formula (II) is a typical example of the known antineoplastic diarylsulfonylurea compounds and it has progressed to Phase I clinical trials(see, *Cancer Res.*, 49, 5217–5220, 1989):

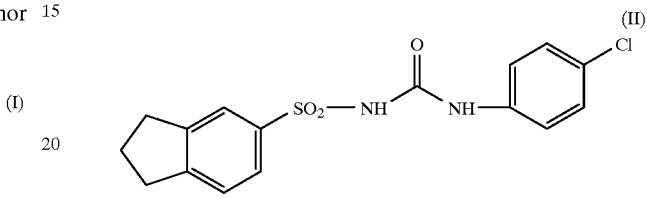

Particularly, it has been reported that this compound exhibits potent antitumor activity upon solid tumors which is hard to cure(see, *J. Med. Chem.*, 1990, 33, 2393). Although the mechanism of action of this compound has not known yet, it has an exceptionally broad spectrum of activity upon solid tumors and human tumor xenogafts and also has some other clinical activities. Moreover, Sulofenur does not produce serious side effects including myelosuppression, nausea, vomiting, alopecia, mucositis, and hepatotoxicity which may be commonly encountered when other antineoplastic agents are used, but only shows minor side effects such as anemia or methemoglobinemia which are originated from aniline class of metabolite.

DISCLOSURE OF THE INVENTION

Those results aforementioned led the present inventors to investigate new arylsulfonylurea derivatives which have more improved antineoplastic activity against solid tumors than Sulofenur and do not produce the aniline class of metabolite which is causative of the side effects as mentioned above. And as a result, the present inventors have identified that the arylsulfonylimidazolone derivative of formula (I) as defined above can satisfies such purpose, and thus completed the present invention. Therefore, it is an object of the present invention to provide a novel arylsulfonylimidazolone derivative represented by the following formula (I):

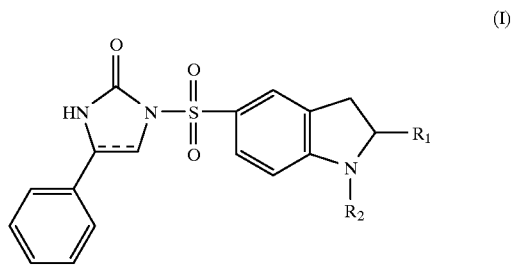

or its pharmaceutically acceptable salt or stereoisomer, in which

= represents single or double bond,

R₁ represents hydrogen or methyl,

R₂ represents chloroacetyl; $C_1$–$C_5$alkylaminoacetyl; allylaminoacetyl; $C_1$–$C_4$ alkoxycarbonyl; nicotinyl; furanoyl; thiophenoyl; benzoyl which can be substituted by halogen, nitro, cyano, amino which can be substituted by nonpolar amino acid residue, hydroxy, methyl or methoxy which can be independently of one another substituted by halogen, ethoxy or chloroacetylamino; or

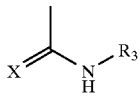

(wherein, X represents oxygen or sulfur atom, R₃ represents $C_1$–$C_4$alkyl, allyl, chloroacetyl or cyclohexyl, or phenyl which can be substituted by methoxy, fluoro, methyl, amino or methylthio).

In the definitions for the substituents of the compound of formula (I), the term "alkyl" which is used alone or in the form of a composite term such as "alkylaminoacetyl" means a straight or branched, saturated hydrocarbon, for example, methyl, ethyl, propyl, isopropyl, isobutyl, t-butyl or its isomers, etc.; the term "alkoxy" which is used alone or in the form of a composite term such as "alkoxycarbonyl" means a straight or branched alkoxy group, for example, methoxy, ethoxy, propoxy, n-butoxy or its isomers, etc; the term "halogen" means fluoro or chloro. In addition, the term "nonpolar amino acid residue" means an amino acid residue having a nonpolar side chain, for example, aminoacetyl, 2-aminopropanoyl, 2-amino-3-methylbutytyl, 2-amino-4-methylpentanoyl, 2-amino-4-methylthiobutyryl, pyrrolidin-2-ylcarbonyl, 2-amino-3-phenylpropanoyl, etc.

It is another object of the present invention to provide a process for preparing a novel arylsulfonylimidazolone derivative of formula (I) or its pharmaceutically acceptable salt or stereoisomer, wherein a) a compound represented by the following formula (III):

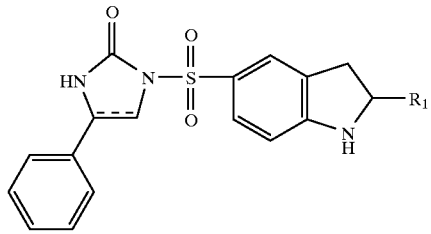

(III)

is reacted with a compound represented by the following formula (IV):

$$R_2\text{—}Y \qquad (IV)$$

to provide the compound represented by the following formula (I):

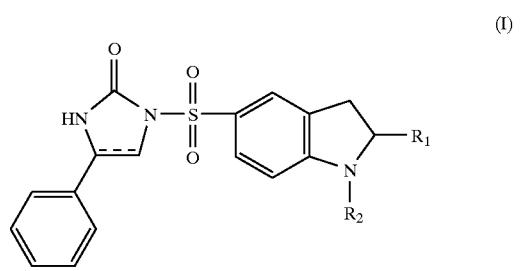

(I)

in the above formulas, R₁ and R₂ are each as previously defined, and Y represents a reactive leaving group; or b) a compound represented by the following formula (III) or its salt:

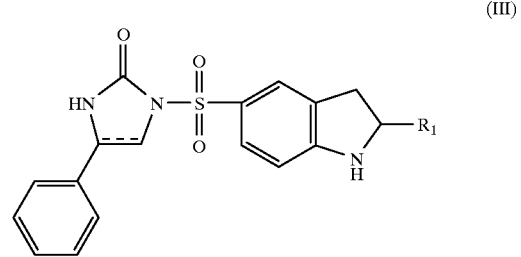

(III)

is reacted with a compound represented by the following formula (V)

$$R_3NC\!=\!X \qquad (V)$$

to provide a compound represented by the following formula (Ia):

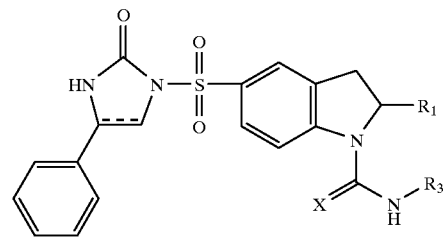

(Ia)

in the above formulas, R₁, R₃ and X are each as previously defined; or c) a compound represented by the following formula (Ib) having a p-nitrobenzoyl group at 1-position of indoline group:

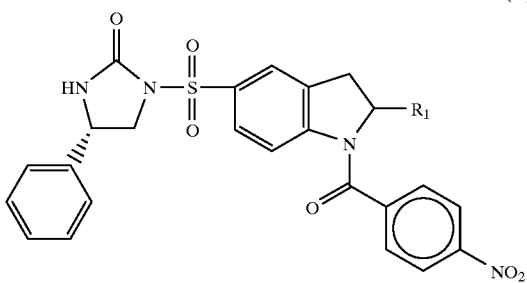

is reduced to provide a compound represented by the following formula (Ic):

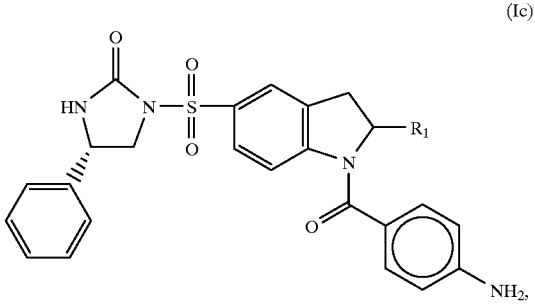

the compound of formula (Ic) or its salt thus prepared is condensed with an amino acid wherein the amino group is protected by t-butoxycarbonyl represented by the following formula (VI):

R$_4$—tBOC         (VI), and then deprotected to provide a compound represented by the following formula (Id):

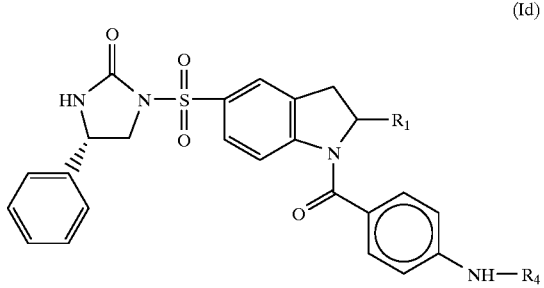

in the above formulas, tBOC represents t-butoxycarbonyl and R$_4$ represents nonpolar amino acid residue.

The compound of formula (III) used as a starting material in the above methods (a) and (b) is itself a novel compound. Therefore, providing the compound of formula (III) with a process for preparation thereof is also another object of the present invention.

It is yet further object of the present invention to provide an antitumor composition that comprises as an active ingredient a therapeutically effective amount of a compound of formula (I) as defined above together with a pharmaceutically acceptable carrier.

BEST MODE FOR CARRYING OUT THE INVENTION

Among the compound of formula (I) according to the present invention, preferred compound includes those wherein a) ═══ is single or double bond, R$_1$ is hydrogen or methyl, and R$_2$ is chloroacetyl; C$_1$–C$_5$alkylaminoacetyl; allylaminoacetyl; C$_1$–C$_4$alkoxycarbonyl; nicotinyl; furanoyl; thiophenoyl; or benzoyl which can be substituted by halogen, nitro, cyano, hydroxy, methyl or methoxy which can independently of one another be substituted by halogen, ethoxy or chloroacetylamino, b) ═══ is single or double bond, R$_1$ is hydrogen, and R$_2$ is

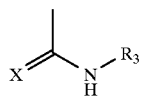

(wherein, X is oxygen or sulfur atom, and R$_3$ is C$_1$–C$_4$alkyl, allyl, chloroacetyl or cyclohexyl, or phenyl which can be substituted by methoxy, fluoro, methyl, amino or methylthio), and c) ═══ is single bond, R$_1$ is hydrogen, R$_2$ is

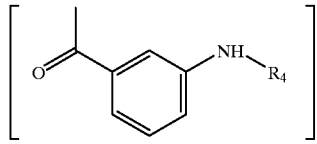

(wherein, R$_4$ is hydrogen or nonpolar amino acid residue), and having (S)-stereoisomeric configuration at 4-carbon of imidazolone ring bearing the phenyl group.

Typical examples of the compound represented by formula (I) include:
4-phenyl-1-(N-ethoxycarbonylindoline-5-sulfonyl)-2-imidazolone;
4-phenyl-1-(N-ethylcarbamoylindoline-5-sulfonyl)-2-imidazolone;
4-phenyl-1-(N-ethylcarbamoyl-2-methylindoline-5-sulfonyl)-2-imidazolone;
4-phenyl-1-(N-propylcarbamoylindoline-5-sulfonyl)-2-imidazolone;
4-phenyl-1-(N-propylcarbamoyl-2-methylindoline-5-sulfonyl)-2-imidazolone;
4-phenyl-1-(N-isopropylcarbamoylindoline-5-sulfonyl)-2-imidazolone;
4-phenyl-1-(N-isopropylcarbamoyl-2-methylindoline-5-sulfonyl)-2-imidazolone;
4-phenyl-1-(N-t-butylcarbamoylindoline-5-sulfonyl)-2-imidazolone;
4-phenyl-1-[N-(4-nitrobenzoyl)indoline-5-sulfonyl]-2-imidazolone;
4-phenyl-1-[N-(4-aminobenzoyl)indoline-5-sulfonyl]-2-imidazolone.HCl;
4-phenyl-1-[N-(4-nitrobenzoyl)-2-methylindoline-5-sulfonyl]-2-imidazolone;
4-phenyl-1-[N-(4-aminobenzoyl)-2-methylindoline-5-sulfonyl]-2-imidazolone.HCl;
4-phenyl-1-(N-benzoylindoline-5-sulfonyl)-2-imidazolone;

4-phenyl-1-[N-(4-ethoxybenzoyl)indoline-5-sulfonyl]-2-imidazolone;
4-phenyl-1-(N-nicotinylindoline-5-sulfonyl)-2-imidazolone;
4-phenyl-1-(N-furanoylindoline-5-sulfonyl)-2-imidazolone;
4-phenyl-1-(N-thiophenoylindoline-5-sulfonyl)-2-imidazolone;
4-phenyl-1-[N-(4-chlorobenzoyl)indoline-5-sulfonyl]-2-imidazolone;
4-phenyl-1-[N-(4-chloroacetylaminobenzoyl)indoline-5-sulfonyl]-2-imidazolone;
4-phenyl-1-[N-(4-chloroacetylaminobenzoyl)-2-methylindoline-5-sulfonyl]-2-imidazolone;
4-phenyl-1-(N-chloroacetyl-2-methylindoline-5-sulfonyl)-2-imidazolone;
4-phenyl-1-(N-methylaminoacetyl-2-methylindoline-5-sulfonyl)-2-imidazolone.HCl;
4-phenyl-1-(N-isopropylaminoacetyl-2-methylindoline-5-sulfonyl)-2-imidazolone.HCl;
4-phenyl-1-(N-isopropylaminoacetylindoline-5-sulfonyl)-2-imidazolone.HCl;
4-phenyl-1-(N-isobutylaminoacetyl-2-methylindoline-5-sulfonyl)-2-imidazolone.HCl;
4-phenyl-1-(N-isobutylaminoacetylindoline-5-sulfonyl)-2-imidazolone.HCl;
4-phenyl-1-(N-t-butylaminoacetyl-2-methylindoline-5-sulfonyl)-2-imidazolone.HCl;
4-phenyl-1-(N-allylaminoacetyl-2-methylindoline-5-sulfonyl)-2-imidazolone.HCl;
4-phenyl-1-(N-ethylcarbamoylindoline-5-sulfonyl)-4,5-dihydro-2-imidazolone;
4-phenyl-1-(N-propylcarbamoylindoline-5-sulfonyl)-4,5-dihydro-2-imidazolone;
4-phenyl-1-(N-isopropylcarbamoylindoline-5-sulfonyl)-4,5-dihydro-2-imidazolone;
4-phenyl-1-(N-allylcarbamoylindoline-5-sulfonyl)-4,5-dihydro-2-imidazolone;
4-phenyl-1-(N-cyclohexylcarbamoylindoline-5-sulfonyl)-4,5-dihydro-2-imidazolone;
4-phenyl-1-(N-phenylcarbamoylindoline-5-sulfonyl)-4,5-dihydro-2-imidazolone;
4-phenyl-1-[N-(4-aminophenyl)carbamoylindoline-5-sulfonyl]-4,5-dihydro-2-imidazolone;
4-phenyl-1-[N-(4-methoxyphenyl)carbamoylindoline-5-sulfonyl]-4,5-dihydro-2-imidazolone;
4-phenyl-1-[N-(4-methylthiophenyl)carbarnoylindoline-5-sulfonyl]-4,5-dihydro-2-imidazolone;
4-phenyl-1-(N-methylthiocarbamoylindoline-5-sulfonyl)-4,5-dihydro-2-imidazolone;
4-phenyl-1-(N-ethylthiocarbamoylindoline-5-sulfonyl)-4,5-dihydro-2-imidazolone;
4-phenyl-1-(N-propylthiocarbamoylindoline-5-sulfonyl)-4,5-dihydro-2-imidazolone;
4-phenyl-1-(N-butylthiocarbamoylindoline-5-sulfonyl)-4,5-dihydro-2-imidazolone
4-phenyl-1-(N-phenylthiocarbamoylindoline-5-sulfonyl)-4,5-dihydro-2-imidazolone;
4-phenyl-1-[N-(4-methoxyphenyl)thiocarbamoylindoline-5-sulfonyl]-4,5-dihydro-2-imidazolone;
4-phenyl-1-[N-(2-methoxyphenyl)carbamoylindoline-5-sulfonyl]-4,5-dihydro-2-imidazolone;
4-phenyl-1-[N-(4-methylphenyl)carbamoylindoline-5-sulfonyl]-4,5-dihydro-2-imidazolone;
4-phenyl-1-[N-(4-fluorophenyl)thiocarbamoylindoline-5-sulfonyl]-4,5-dihydro-2-imidazolone;
4-phenyl-1-(N-benzoylindoline-5-sulfonyl)-4,5-dihydro-2-imidazolone;
4-phenyl-1-[N-(4-methylbenzoyl)indoline-5-sulfonyl]-4,5-dihydro-2-imidazolone;
4-phenyl-1-[N-(2-hydroxybenzoyl)indoline-5-sulfonyl]-4,5-dihydro-2-imidazolone;
4-phenyl-1-[N-(4-methoxybenzoyl)indoline-5-sulfonyl]-4,5-dihydro-2-imidazolone;
4-phenyl-1-[N-(3,4-dimethoxybenzoyl)indoline-5-sulfonyl]-4,5-dihydro-2-imidazolone;
4-phenyl-1-[N-(4-ethoxybenzoyl)indoline-5-sulfonyl]-4,5-dihydro-2-imidazolone;
4-phenyl-1-[N-(4-chlorobenzoyl)indoline-5-sulfonyl]-4,5-dihydro-2-imidazolone;
4-phenyl-1-[N-(4-fluorobenzoyl)indoline-5-sulfonyl]-4,5-dihydro-2-imidazolone;
4-phenyl-1-[N-(4-nitrobenzoyl)indoline-5-sulfonyl]-4,5-dihydro-2-imidazolone;
4-phenyl-1-[N-(4-cyanobenzoyl)indoline-5-sulfonyl]-4,5-dihydro-2-imidazolone;
4-phenyl-1-[N-(4-aminobenzoyl)indoline-5-sulfonyl]-4,5-dihydro-2-imidazolone.HCl;
4-phenyl-1-[N-(3-chlorobenzoyl)indoline-5-sulfonyl]-4,5-dihydro-2-imidazolone;
4-phenyl-1-[N-(3,5-dichlorobenzoyl)indoline-5-sulfonyl]-4,5-dihydro-2-imidazolone;
4-phenyl-1-[N-(3-fluorobenzoyl)indoline-5-sulfonyl]-4,5-dihydro-2-imidazolone;
4-phenyl-1-[N-(2,4-difluorobenzoyl)indoline-5-sulfonyl]-4,5-dihydro-2-imidazolone;
4-phenyl-1-[N-(3-trifluoromethylbenzoyl)indoline-5-sulfonyl]-4,5-dihydro-2-imidazolone;
4-phenyl-1-[N-(3-trifluoromethoxybenzoyl)indoline-5-sulfonyl]-4,5-dihydro-2-imidazolone;
4-phenyl-1-[N-(4-trifluoromethoxybenzoyl)indoline-5-sulfonyl]-4,5-dihydro-2-imidazolone;
(S)-(+)-4-phenyl-1-[N-(4-aminobenzoyl)indoline-5-sulfonyl]-4,5-dihydro-2-imidazalone.HCl;
(S)-(+)-4-phenyl-1-[N-{4-(2-aminopropanoyl)aminobenzoyl}indoline-5-sulfonyl]-4,5-dihydro-2-imidazolone.HCl;
(S)-(+)-4-phenyl-1-[N-{4-(2-aminoacetyl)aminobenzoyl}indoline-5-sulfonyl]-4,5-dihydro-2-imidazolone.HCl;
(S)-(−)-4-phenyl-1-[N-{4-(2-amino-3-phenyl-propanoyl)aminobenzoyl}indoline-5-sulfonyl]-4,5-dihydro-2-imidazolone.HCl.

The most preferred compounds among those exemplified above are 4-phenyl-1-(N-isopropylcarbamoylindoline-5-sulfonyl)-2-imidazolone and (S)-(+)-4-phenyl-1-[N-(4-aminobenzoyl)indoline-5-sulfonyl]-4,5-dihydro-2-imidazolone.

The compound of the present invention can have an asymmetric carbon atom in their structure, namely the 4-carbon atom of the imidazolone ring bearing the phenyl group. Said chiral center can be present in the configuration of (R) or (S), or a mixture of (R) and (S). Thus, the present invention also includes all those stereoisomers and their mixtures. Particularly, in the present invention, more preferred stereoisomeric configuration is (S).

The compound of formula (I) according to the present invention can form a pharmaceutically acceptable salt. In the present specification, the term "pharmaceutically acceptable salt" means "non-toxic acid addition salt" and such salt includes a salt with inorganic acids such as hydrochloric acid, hydrobromic acid, phosphoric acid, sulfuric acid, etc., a salt with organic acids such as acetic acid, oxalic acid, p-toluenesulfonic acid, methanesulfonic acid, citric acid, fumaric acid, succinic acid, tartaric acid, ascorbic acid, etc., and a salt with other acids which are generally known and conventionally used in the technical field of imidazoline-based compounds. These acid-addition salts can be prepared in situ during the final isolation and purification of the compound of formula (I), or can be prepared separately by reacting the free form compound with a corresponding acid according to a conventional conversion method.

According to the present invention, the compound of formula (I) can be prepared by any method depicted in the following reaction schemes (a) to (c), which will be explained in detail.

Reaction Scheme (a)

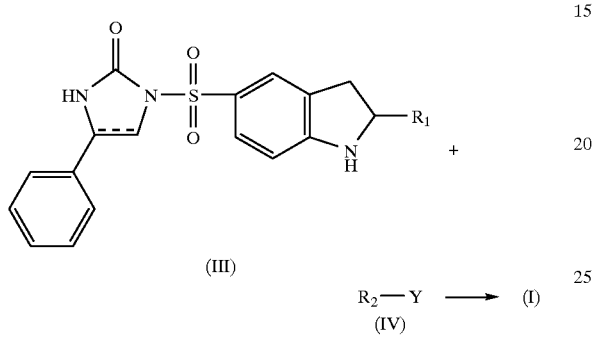

In the reaction of the compound of formula (III) with the compound of formula (IV) according to the reaction scheme (a) above, any reaction-inert organic solvent may be used unless it adversely affects the reaction. Solvents suitable for this reaction include benzene, toluene, dichloromethane, tetrahydrofuran, chloroform, methanol and ethanol. Among those, dichloro-methane or tetrahydrofuran can be preferably used. This reaction may also be carried out in the presence of a base. As the base, pyridine, dimethylaminopyridine, triethylamine or diethylamine, preferably pyridine can be used. Reaction temperature and time are not restricted specifically, and can be determined depending on the starting materials used. Generally, this reaction may be carried out at room temperature for 1 to 8 hours.

Reaction Scheme (b)

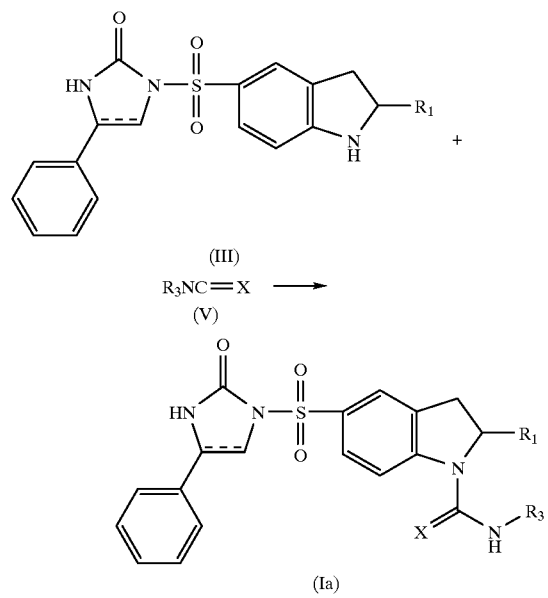

The reaction of the compound of formula (III) with the compound of formula (V) to prepare the compound of formula (Ia) wherein the nitrogen of the indoline ring is substituted by carbamoyl or thiocarbamoyl group, may be carried out in a solvent. As the solvent, benzene, toluene or dimethylformamide, preferably toluene can be used. Reaction temperature and time are not restricted specifically as in the reaction (a) above, however, this reaction can be generally carried out at 50 to 80° C. for 5 to 18 hours.

Reaction Scheme (c)

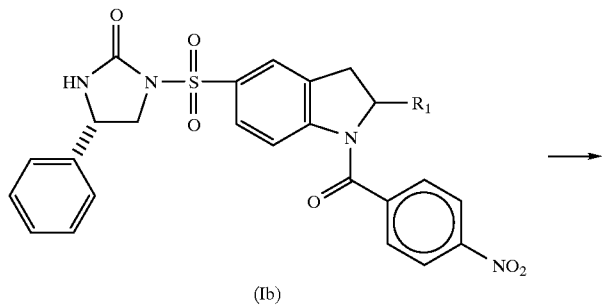

-continued

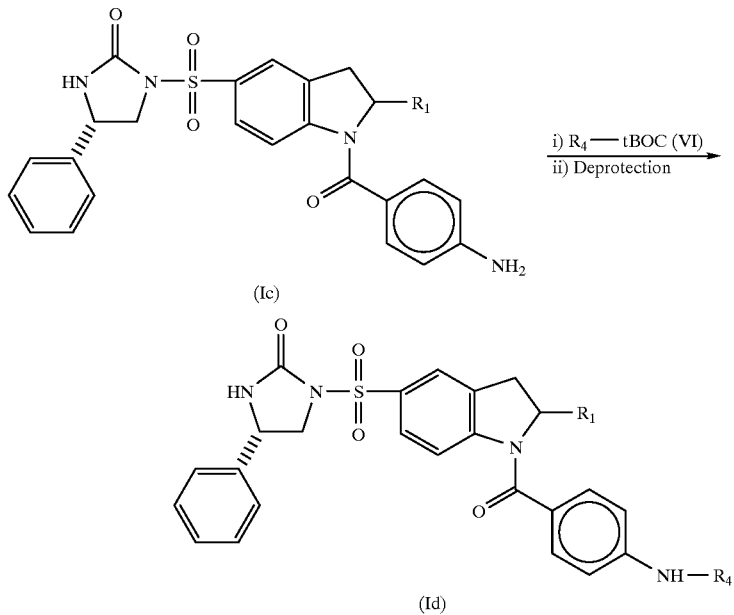

In the first step of the reaction (c), the nitro group of the compound of formula (Ib) which has an asymmetric centor in the imidazolone ring and thus has (S)-stereospecificity, is reduced to amino group to prepare the compound of formula (Ic). Reduction may be carried out under conventional reducing conditions, for example, under the presence of iron and methanol, Raney nickel and hydrogen gas, or sodium-borohydride and palladium.

In the second step of the reaction (c), the condensation product obtained by reacting the compound of formula (Ic) with the subsitituted amino acid of formula (VI) is subsequently deprotected to produce the desired compound of formula (Id) having (S)-stereospecificity. As the compound of formula (VI), L-form amino acid which is the form generally occurred in human body is used. Conventional reaction conditions for removing protecting groups may be used for the deprotection reaction. For example, the deprotection can be carried out in the presence of trifluoroacetic acid (TFA) and p-cresol. This second reaction step may be easily carried out by referring to the known method disclosed in J. Med. Chem., 1996, 39, 3114–3122.

When the compound of formula (I) having (S)-stereoisomeric configuration is desired, (S)-stereoisomeric starting materials may be used.

After the desired product is obtained according to the processes (a) to (c), it may be recovered and purified, if desired, by any methods known to those skilled in the art, such as filtration, chromatography or crystallization.

While, the starting material of formula (III) used in reaction processes (a) and (b) is itself novel. Therefore, the present invention provides the compound (III) as an useful intermediate for preparing the compound (I).

The compound of formula (III) can be obtained by anyone of processes (d) to (f), wherein d) a compound represented by the following formula (VIIa):

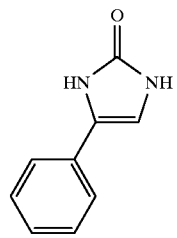

(VIIa)

is reacted with a compound represented by the following formula (VIII):

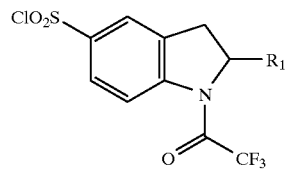

(VIII)

to provide a compound represented by the following formula (IXa):

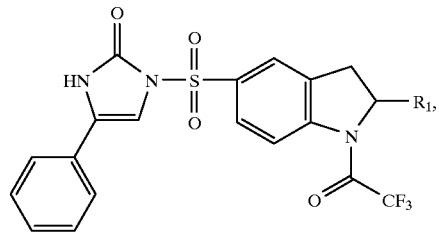

(IXa)

then the trifluoroacetyl group as an amino-protecting group of the compound of fomula (IXa) is removed to prepare the compound represented by the following formula (IIIa):

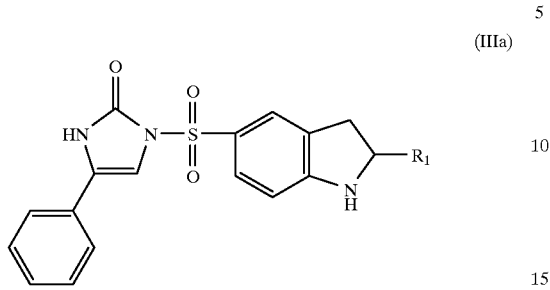

(IIIa)

in the above formulas, $R_1$ is as previously defined; or e) a compound represented by the following formula (VIIb):

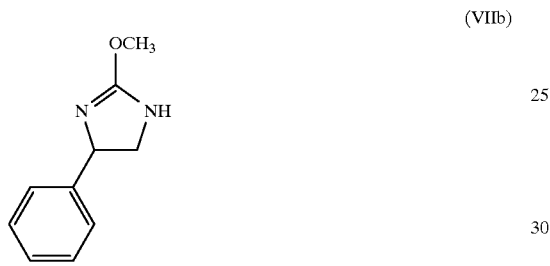

(VIIb)

is reacted with a compound represented by the following formula (VIII):

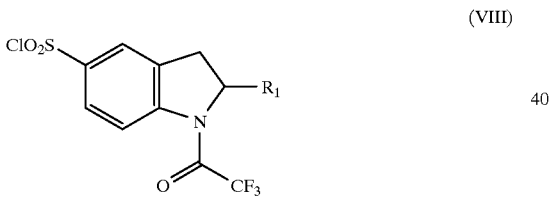

(VIII)

to provide a compound represented by the following formula (IXb):

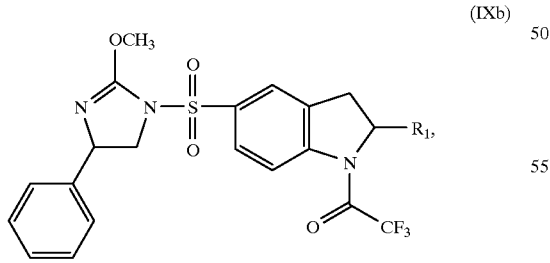

(IXb)

then the trifluoroacetyl group of the compound of fomula (IXb) is removed and the product thus obtained is acid-hydrolyzed to prepare the compound represented by the following formula (IIIb):

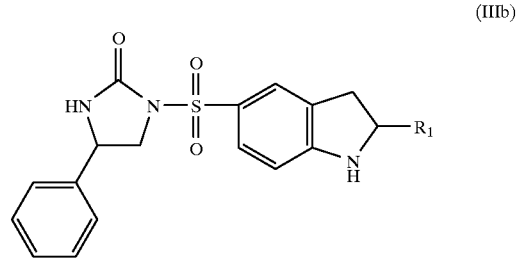

(IIIb)

in the above formulas, $R_1$ is as previously defined; or f) (S)-phenylglycinol represented by the following formula (X):

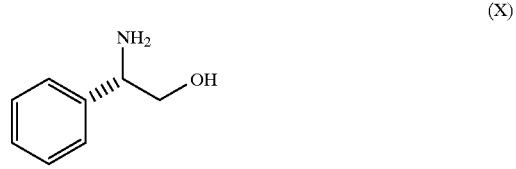

(X)

is reacted with phenylchloroformate (ClCOOPh) to provide a compound represented by the following formula (XI):

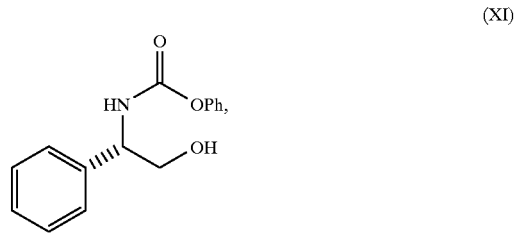

(XI)

which is reacted with methanesulfonylchloride ($CH_3SO_2Cl$) to produce a compound represented by the following formula (XII):

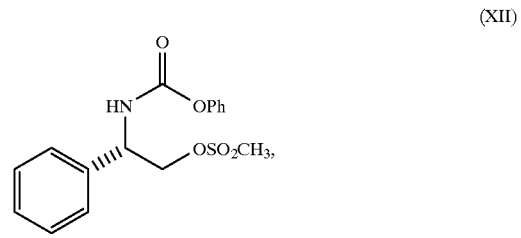

(XII)

then the compound of formula (XII) thus obtained is combined with a compound represented by the following formula (XIII):

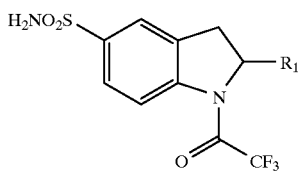

and deprotected to provide a compound represented by the following formula (IIIc):

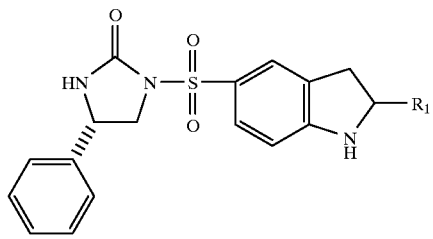

in the above formulas, R₁ is as previously defined.

The above methods (d) to (f) for preparing the compound (III) can be depicted as the following reaction schemes (d) to (f), respectively, which will be explained in detail.

Reaction Scheme (d)

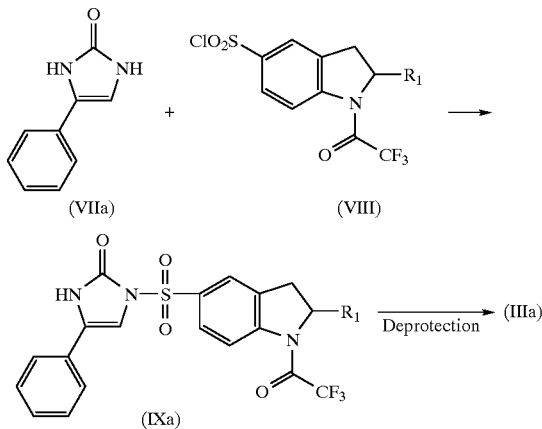

In the first step of the reaction (d), the compounds of formula (VIIa) and (VIII) are coupled to produce the compound (IXa). These starting compounds (VIIa) and (VIII) can be synthesized by conventional methods known in the art (see, Drug Res., 42, pp592–594, 1992; Chimie Therapeutique, 6, pp659–668, 1973). This reaction may be carried out in an aprotic organic solvent and in the presence of a base. Solvents which can be suitably used for the reaction include dimethylformamide, N-methylpyrrolidone, acetonitrile, dimethylsulfoxide, benzene, tetrahydrofuran and the like. Dimethylformamide is the most preferable one. As the base, potassium carbonate, sodium carbonate, sodium methoxide, patassium t-butoxide, sodium hydride, etc, preferably sodium hydride can be mentioned. Generally, the two reactants are used in an equimolar amount to each other although one can be used in an excessive amount with respect to the other, and the present reaction is carried out at 0° C. to the boiling point of the reaction mixture, preferably at 20 to 30° C. The reaction is somewhat exothermic and usually completed within 5 to 6 hours.

In the deprotection step, the trifluoroacetyl group is removed by suspending the compound of formula (IXa) in a solvent mixture of water and methanol and then reacting the suspension with potassium carbonate to produce the compound of formula (IIIa). However, the deprotection reaction can also be carried out according to conventional methods known in the art (see, J. Org. Chem., 53, 3108, 1988; J. Am. Chem. Soc., 95, 612, 1973).

Reaction Scheme (e)

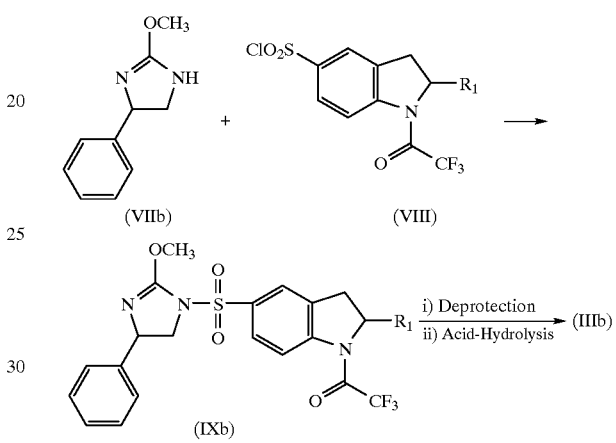

In the first step, the starting compounds (VIIb) and (VIII) which can be obtained by conventional methods known in the art (see, J. Am. Chem. Soc., 107, pp2931–2943, 1992; Chimie Therapeutique, 6, pp659–668, 1973) are coupled to produce the compound (IXb). This reaction can be carried out in a water miscible inert solvent such as tetrahydrofuran or acetone in the presence of a base such as potassium carbonate, sodium carbonate, lithium hydroxide or sodium bicarbonate, preferably sodium bicarbonate. Generally, the two reactants are used in an equimolar amount to each other or slight molar excess of compound (VIII) is used with respect to compound (VIIb) although other ratios are also operative. The present reaction is carried out at 0 to 80° C., preferably at 20 to 30° C. At these preferable temperature, the reaction is usually completed within about 4 hours.

The deprotection reaction can be performed according to the same manner as described in method (d). Then, the acid-hydrolysis is carried out according to conventional methods known in the art.

Reaction Scheme (f)

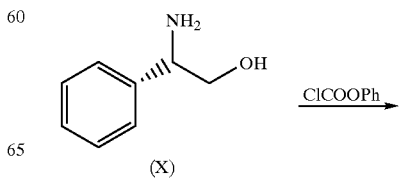

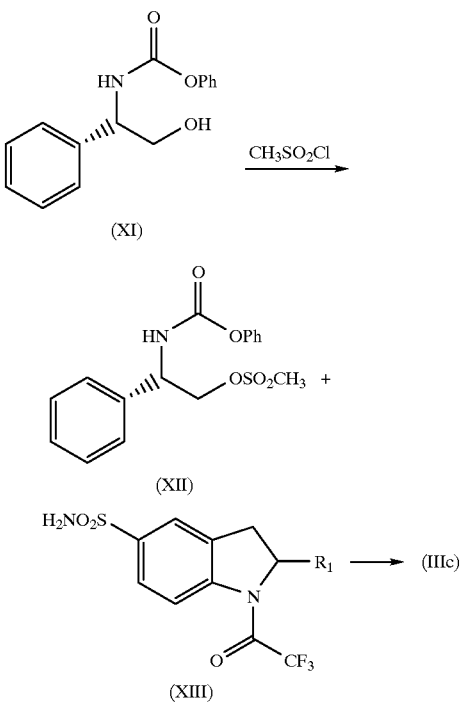

In the first reaction step, the commercially available (S)-2-phenylglycinol is dissolved in distilled water together with a base selected from a group consisting of sodium carbonate, sodium bicarbonate and potassium bicarbonate, and then to this reaction mixture is slowly added dropwise phenylchloroformate dissolved in a small amount of tetrahydrofuran. After the reaction is carried out at room temperature for one hour, the product is extracted with ethyl acetate to obtain the (S)-2-N-phenoxycarbonylamino-2-phenylethanol of formula (XI).

The compound (XI) thus produced is dissolved in a solvent of chloroform, tetrahydrofuran or methylene chloride, cooled down to 0° C., and then reacted with methanesulfonylchloride in the presence of a base of pyridine or triethylamine to obtain the (S)-2-N-phenoxycarbonylamino-2-phenylethyl methanesulfonate of formula (XII).

Finally, the compound (XII) thus produced is reacted with the known N-trifluoroacetyl-5-aminosulfonyl-indoline of formula (XIII) to prepare the compound of formula (IIIc). The compound of formula (XIII) used as a reactant in this reaction can be prepared by an art-known procedure (see, *Chimie Therapeutique*, 6, 659–668, 1973). As the solvent suitable for the reaction of compounds (XII) with (XIII), an aprotic solvent such as, for example, benzene, chloroform, dimethylsulfoxide, dimethylformamide, tetrahydrofuran, methylethylketone, etc., preferably dimetylformamide can be mentioned. In some instances, the addition of a suitable base such as, for example, potassium carbonate, sodium methoxide, sodium carbonate, potassium t-butoxide, sodium hydride, etc., particularly sodium hydride may be appropriate. The same molar ratio of reactants, reaction temperature and time as the first step of reaction (d) may be applied for this reaction.

In view of their potent antineoplastic activities, the desired compound of formula (I) according to the present invention may be formulated into pharmaceutical compositions for administration purposes. Said pharmaceutical compositions are deemed novel and consequently constitutes a further aspect of the present invention. Therefore, the present invention also relates to an antitumor composition comprising a pharmaceutically acceptable carrier and as an active ingredient a therapeutically effective amount of a compound of formula (I), as defined above.

The pharmaceutical composition according to the present invention may be administered orally, rectally, parenterally (i.e., intravenously, intramuscularly or subcutaneously), intracisternally, intravaginally, intraperitoneally or locally for the treatment of susceptible neoplasms. Oral preparations of solid dosage form may include capsules, tablets, pills, powders or granules. In such a solid dosage form for oral administration, the active compound of formula (I) is admixed with at least one excipient such as fillers, binders, humectants, disintegrating agents, solution retarders, absorption accelerators, wetting agents, adsorbents or lubricants. Oral preparations of liquid dosage form may include pharmaceutically acceptable emulsions, solutions, suspensions, syrups and elixirs. In addition to the active ingredient, the liquid dosage form may contain inert diluents commonly used in the art, such as water, other solvents, solubilizing agents, suspending agents or emulsifiers. The injectable preparation for parenteral administration may be in the form of water, water-polyethyleneglycol or water-propyleneglycol solution, of which isotonicity, pH, fluidity and the like can be adjusted to be suited for the physiological condition of living body. The injectable preparation may include sterile aqueous or nonaqueous solutions, dispersions, suspensions, emulsions and ready-to-use injectable preparation. Examples of suitable aqueous or nonaqueous carriers, diluents, solvents or vehicles include water, ethanol, propylene glycol, polyethylene glycol, glycerol, suitable mixtures thereof, vegetable oils(such as corn oil or olive oil) and injectable organic esters such as ethyl oleate. Proper fluidity can be maintained, for example, by the use of a coating agent such as lecithin, by the maintenance of the specified particle size in the case of dispersions, and by the use of surfactants. It is especially advantageous to formulate the aforementioned pharmaceutical preparations in dosage unit form for ease of administration and uniformity of dosage. Dosage unit forms of the preparation refer to physically discrete units suitable as unitary dosage, each unit containing a predetermined quantity of the active component calculated to produce the desired therapeutic effect. Such dosage unit form can be in the packaged form, for example, a tablet, a capsule or a powder filled in vial or ampule, or an ointment, gel or cream filled in tube or bottle.

When the active compound of formula (I) of the present invention is applied as a medicine to a patent suffering from susceptible neoplasm, it is preferably administered in an amount of about 10 to about 5000 mg, preferably about 10 to about 1000 mg. However, the administration dosage can be varied with the requirement of the subject patient, severity of the neoplasm to be treated, the selected compound, the route of administration, the duration of treatment and the like. The preferred dosage suitable for a certain condition can be determined by a person skilled in this art according to a conventional manner. In general, the therapeutic treatment is started from the amount less than the optimal dosage of the active compound and then the administration dosage is increased little by little until the optimal therapeutic effect is obtained. As a matter of convenience, the total daily dosage can be divided into several portions and administered over several times, for example, once to six times per day.

The present invention will be more specifically explained in the following examples. However, it should be understood that the following preparations and examples are intended to illustrate the present invention and not to limit the scope of the present invention in any manner.

Preparation 1

Synthesis of 4-phenyl-1,3-dihydro-2-imidazolone

2-Bromoacetophenone (18 g, 90 mmol) was dissolved in 900 ml of chloroform. Hexamethylenetetraamine (13.87 g, 99 mmol) was added thereto and the reaction mixture was stirred at 60° C. for 4 hours. After stirring, the reaction mixture was cooled down to room temperature, filtered, and the collected precipitate was suspended in 180 ml of ethanol. To the suspension thus obtained was added dropwise 90 ml of conc. HCl, and the reaction mixture was stirred at room temperature for 18 hours. Then, the reaction mixture was filtered to remove a white precipitate, the filtrate was concentrated under reduced pressure to obtain a yellow solid. This solid was recrystallized from a mixture of methanol and ethyl acetate (1:50, v/v) to obtain 13 g of 2-aminoacetophenone as a yellow solid.

Yield: 84%

$^1$H NMR(DMSO-$d_6$): 4.45(s,2H), 7.5–7.8(m,4H), 8.64(brs, 2H), 8.68(s,1H)

2-Aminoacetophenone (5.6 g, 32.65 mmol) was dissolved in 200 ml of water in a three necked flask equipped with a thermometer and was heated up to 70° C. Potassium cyanate (2.9 g, 35.92 mmol) was added in several portions at 70° C. while the pH of the reaction solution was maintained in the range of 1 to 3 by the continuous addition of conc. HCl. After the addition of potassium cyanate was completed, the reaction mixture was stirred at 70° C. for 4 hours and left at room temperature overnight. The brownish precipitate thus formed was collected by filtration and dried to obtain 3.7 g of the title compound.

yield: 72%

$^1$H NMR(DMSO-$d_6$): 6.90(s,1H), 7.2–7.6(m,5H), 10.02(s, 1H), 10.49(s,1H)

Preparation 2

Synthesis of N-trifluoroacetyl-2-methylindoline-5-sulfonylchloride

2-Methylindoline (10 ml, 76.8 mmol) was dissolved in 100 ml of dichloromethane and then cooled down to 0° C. To this solution were added pyridine (18.7 ml, 0.22 mol) and trifluoroacetic anhydride (24 ml, 0.17 mol). The reaction mixture was stirred at room temperature for 6 hours, diluted with 300 ml of dichloromethane, and then washed twice with 150 ml of 5% HCl. The dichloromethane layer was dried over anhydrous magnesium sulfate, and concentrated to obtain 15 g of N-trifluoroacetyl-2-methyl-indoline.

Yield: 85%

Chlorosulfonic acid (25 ml, 0.37 mmol) was cooled down to 0° C. in a three necked flask equipped with a thermometer. N-trifluoroacetyl-2-methyl-indoline (17 g, 74.23 mmol) was added thereto in several portions. After the resulting mixture was stirred at 60° C. for 1 hour, the reaction mixture was slowly poured into 200 ml of ice water. The precipitate thus formed was collected by filtration and dried to afford 9.2 g of the title compound.

Yield: 80%

$^1$H NMR(DMSO-$d_6$): 1.20(d,J=6.9 Hz,3H), 2.75–2.79(m, 1H), 3.39–3.45(m,1H), 4.81–4.84(m, 1H), 7.48–7.58(m, 2H), 7.95(d,J=8.3 Hz, 1H)

N-trifluoroacetyl-indoline-5-sulfonylchloride can also be prepared according to the same procedure except that indoline instead of 2-methylindoline is used as a starting material.

Preparation 3

Synthesis of 4-phenyl-1-(indoline-5-sulfonyl)-2-imidazolone

4-Phenyl-2,3-dihydro-1H-2-imidazolone (4 g, 24.84 mmol) prepared in Preparation 1 was suspended in 30 ml of dimethylformamide and cooled down to 0° C. After sodium hydride (60% oily, 1.09 g, 27.3 mmol) was added thereto, the resulting mixture was stirred for a few minutes at 0° C. until it became a clear solution. To the reaction mixture was added portionwise at 0° C. the N-trifluoroacetyl-indoline-5-sulfonylchloride (8.56 g, 27.32 mmol) prepared in Preparation 2. The reaction mixture was stirred at room temperature for 4 hours, cooled down again to 0° C., and then water was slowly added to the mixture until precipitate was formed. The resulting precipitate was collected, washed with water, and dried to afford 7.6 g of 4-phenyl-1-(N-trifluoroacetylindoline-5-sulfonyl)-2-imidazolone.

4-Phenyl-1-(N-trifluoroacetylindoline-5-sulfonyl)-2-imidazolone (6 g, 13.3 mmol) thus obtained was suspended in 30 ml of a mixture of water and methanol (1:1, v/v). Potassium carbonate (3.7 g, 26.6 mmol) was added to the suspension and the reaction mixture was stirred at room temperature for 4 hours. After stirring, the reaction mixture was concentrated to a half volume. The crude product thus obtained was extracted twice with 200 ml of dichloromethane, washed with brine, dried over anhydrous magnesium sulfate, concentrated to an oily state, and then crystallized from ethyl acetate to afford 4.08 g of the title compound as a white solid.

Yield: 87%

$^1$H NMR (DMSO-$d_6$): 3.01(t,J=8.76 Hz,2H), 3.56(t,J=8.8 Hz,2H), 6.47(d,J=6.12 Hz,1H), 6.95(s,1H), 7.25–7.63(m, 8H), 11.09(s,1H)

4-Phenyl-1-(2-methylindoline-5-sulfonyl)-2-imidazolone can also be prepared according to the same procedure except that N-trifluoroacetyl-2-methylindoline-5-sulfonylchloride instead of N-trifluoroacetyl-indoline-5-sulfonylchloride is reacted.

Preparation 4

Synthesis of 2-methoxy-4-phenyl-4,5-dihydro-2-imidazole

N-bromosuccinimide (10.68 g, 0.06 mol) and cyanamide (4.2 g, 0.1 mol) were dissolved in 150 ml of dichloromethane and the mixture was stirred for 5 min. To this mixture was added a solution of styrene (5.2 g, 0.05 mol) in 20 ml of dichloromethane using a dropping funnel for one hour. The resulting reaction mixture was stirred at room temperature for 12 hours, washed with an equal volume of 5% sodium thiosulfate and brine which were freshly prepared, dried over anhydrous magnesium sulfate, concentrated, and then purified by silica gel column chromatography (eluent ethylacetate/toluene=1/20, v/v) to afford 8.98 g of 2-bromo-1-phenylethyl cyanamide.

Yield: 64%

2-Bromo-1-phenylethylcyanamide (4.5 g, 0.02 mol) thus obtained was dissolved in 16 ml of 7%(w/w) HCl—CH$_3$OH solution and the resulting mixture was stirred at 35 to 40° C. for 6 hours. After the reaction mixture was cooled down to room temperature, sodium carbonate (5.3 g, 0.05 mol) was added thereto and the reaction mixture was stirred overnight at room temperature. Then, water (200 ml) was added, the product was extracted with dichloromethane, dried over anhydrous magnesium sulfate, concentrated and purified by recrystallization from ethylacetate to afford 2.6 g of the title compound as a white solid.

Yield: 74%

$^1$H NMR (CDCl$_3$): 3.45(dd,1H,J=7.9,10.8 Hz), 3.90(s,3H), 4.01(dd,1H,J=9.2, 10.8 Hz), 4.93(dd,1H,J=7.9,9.2 Hz), 7.71 (s,5H)

Preparation 5

Synthesis of 4-phenyl-1-(indoline-5-sulfonyl)-4,5-dihydro-2-imidazolone

2-Methoxy-4-phenyl-4,5-dihydro-2-imidazole (0.95 g, 5 mmol) prepared in Preparation 4 was dissolved in 20 ml of acetone, and then sodium bicarbonate (0.63 g, 7.5 mmol) in 20 ml of water, N-trifluoroacetyl-indoline-5-sulfonylchloride (1 .3 g, 5 mmol) prepared in Preparation 2 were added thereto one after another. After the reaction mixture was stirred at room temperature for 1 hour, the crude product was extracted four times from 20 ml of dichloromethane, dried over anhydrous magnesium sulfate, concentrated, and then purified by silica gel column chromatography (eluent: ethyl acetate/hexane=1/2, v/v) to afford 1.01 g (Yield: 49%) of 2-methoxy-4-phenyl-1-(N-trifluoroacetylindoline-5-sulfonyl)-4,5-dihydro-2-imidazole. The compound thus obtained was treated with 10 ml of 5%(w/w) HCl—CH$_3$OH at room temperature for 3 hours. The resulting precipitate was collected, washed with methanol, and then dried to afford 0.8 g (Yield: 75%) of 4-phenyl-1-(N-trifluoroacetylindoline-5-sulfonyl)-4,5-dihydro-2-imidazolone.

The trifluoroacetyl group of said compound was deprotected according to the same procedure as Preparation 3 to afford the title compound as a white solid.

Yield: 72%

$^1$H NMR (DMSO-d$_6$): 2.98(t,J=8 Hz,2H), 3.33–3.40(m,1H), 3.57(t,J=8 Hz,2H), 4.17(t,J=8.8 Hz, 1H), 4.74(t,J=6.36 Hz, 1H), 6.49(d,J=8.32 Hz,1H), 6.79(s,1H), 7.22–7.47(m,12H), 8.08(s,1H)

Preparation 6

Synthesis of (S)-2-N-phenoxycarbonylamino-2-phenylethylmethanesulfonate (S)-(+)-2-phenylglycinol (1 g, 7.3 mmol) and sodium bicarbonate (0.92 g, 10.95 mmol) were dissolved in 20 ml of water. Phenylchlorofornate (0.92 ml, 7.66 mmol) in 2 ml of THF was slowly added thereto, and the reaction mixture was stirred at room temperature for 1 hour. The resulting product was extracted from 100 ml of ethyl acetate, washed with brine, dried over anhydrous magnesium sulfate, and then concentrated to afford 1.72 g (Yield: 91%) of (S)-2-N-phenoxycarbonylamino-2-phenylethanol as a white solid.

(S)-2-N-phenoxycarbonylamino-2-phenylethanol (2 g, 7.75 mmol) was dissolved in 30 ml of dichloromethane and then cooled down to 0° C. Triethylamine (3.24 ml, 33.25 mmol) and methanesulfonyl chloride (1.2 ml, 15.5 mmol) were added thereto at 0° C. one after another. The whole reaction mixture was stirred at 0° C. for 30 min and then further stirred at room temperature for 1 hour. The reaction mixture was diluted with 50 ml of dichloromethane, washed with brine, dried over anhydrous magnesium sulfate, and then concentrated. The residue was recrystallized from a mixture of methanol and ethyl acetate (1/30, v/v) to afford 2.5 g of the title compound as a white solid.

Yield: 96%

$^1$H NMR (DMSO-d$_6$): 3.20(s,3H), 4.31–4.40(m,2H), 4.96–5.14(m,1H), 6.97–7.46(m,10H), 8.63(d,J=8.76 Hz)

Preparation 7

Synthesis of N-trifluoroacetylindoline-5-sulfonamide

N-trifluoroacetyl-indoline-5-sulfonylchloride (4 g, 13.35 mmol) prepared in Preparation 2 was dissolved in 100 ml of dichloromethane and ammonia gas was passed through the reaction mixture for 2 hours. The precipitate thus formed was collected and dried to afford 3.51 g of the title compound.

Yield: 94%

$^1$H NMR (DMSO-d$_6$): 3.32(t,J=16 Hz,2H), 4.33(t,J=16 Hz,2H), 7.35(s,2H), 7.73–7.76(m,2H), 8.13–8.15(m, 1H)

Preparation 8

Synthesis of (S)-(+)-4-phenyl-1-(indoline-5-sulfonyl)-4,5-dihydro-2-imidazolone

Sodium hydride (60% oily, 475 mg, 11.88 mmol) was suspended in 15 ml of dimethylformamide and cooled down to 0° C. To the suspension was added N-trifluoroacetyl-indoline-5-sulfonamide (0.832 g, 2.97 mmol) prepared in Preparation 7 in several portions, and then the mixture was stirred at 0° C. for 10 min. Then, (S)-2-N-phenoxycarbonylamino-2-phenylethylmethanesulfonate (1.0 g, 2.97 mmol) prepared in Preparation 6 was added thereto. The reaction mixture was stirred at 0° C. for 3 hours and further stirred at room temperature for 1 hour. After confirming the completion of reaction by TLC, the reaction mixture was poured into 30 ml of ice. The resulting precipitate was collected and dried to afford 0.72 g of the title compound.

Yield: 68%

$^1$H NMR (DMSO-d$_6$): 2.98(t,J=8 Hz,2H), 3.33–3.40(m,1H), 3.57(t,J=8 Hz,2H), 4.17(t,J=8.8 Hz, 1H), 4.74(t,J=6.36 Hz, 1H), 6.49(d,J=8.32 Hz,1H), 6.79(s, 1H), 7.22–7.47(m,12H), 8.08(s,1H)

EXAMPLE 1

Synthesis of 4-phenyl-1-(N-ethoxycarbonylindoline-5-sulfonyl)-2-imidazolone

4-Phenyl-1-(indoline-5-sulfonyl)-2-imidazolone (150 mg, 0.44 mmol) prepared in Preparation 3 was dissolved in 10 ml of dichloromethane and then pyridine (39 μl, 0.484 mmol) and ethylchloroformate (46 μl, 0.484 mmol) were added thereto one after another. After the reaction mixture was stirred for one hour at room temperature, it was diluted with dichloromethane and washed twice with brine. The organic layer thus obtained was dried over anhydrous magnesium sulfate, concentrated to an oily state under reduced pressure, and then purified by silica gel column chromatography (eluent:dichloromethane/methanol=15/1, v/v) to afford 173 mg of the title compound as a white solid.

Yield: 96%

M.P.: 214–216° C.

$^1$H NMR(DMSO-d$_6$): 1.17(t,J=4.87 Hz,3H), 3.13–3.18(m, 2H), 3.98–4.03(m,2H), 4.16–4.23(m,2H), 7.19–7.84(m,8H), 11.20(s,1H)

EXAMPLE 2

Synthesis of 4-phenyl-1-(N-ethylcarbamoylindoline-5-sulfonyl)-2-imidazolone

4-Phenyl-1-(indoline-5-sulfonyl)-2-imidazolone (100 mg, 0.29 mmol) prepared in Preparation 3 was dissolved in 10 ml of toluene, and ethylisocyanate (35 µl, 0.435 mmol) was added thereto. The reaction mixture was stirred for 8 hours at 80° C. The solvent was evaporated therefrom under reduced pressure. The residue was dissolved in 30 ml of dichloromethane, washed twice with brine, dried over anhydrous magnesium sulfate, concentrated to an oily state, and then purified by silica gel column chromatography (eluent:dichloromethane/methanol=15/1, v/v) to obtain 113 mg of the title compound.
Yield: 95%
M.P.: 234.1–234.8° C.
$^1$H NMR(DMSO-$d_6$): 1.06(t,J=3.98 Hz,3H), 3.23–3.28(m, 2H), 3.89–4.03(m,2H), 6.93(s,1H), 7.28–7.99(m,8H), 11.16 (s,1H)

EXAMPLE 3

Synthesis of 4-phenyl-1-(N-ethylcarbamoyl-2-methylindoline-5-sulfonyl)-2-imidazolone The title compound was prepared according to a procedure substantially similar to Example 2.
Yield: 92%
M.P.: 239.8–241.4° C.
$^1$H NMR (DMSO-$d_6$): 1.17(t,J=4.87 Hz,3H), 3.13–3.18(m, 2H), 3.98–4.03(m,2H), 4.16–4.23(m,2H), 7.19–7.84(m,8H), 11.20(s,1H)

EXAMPLE 4

Synthesis of 4-phenyl-1-(N-propylcarbamoylindoline-5-sulfonyl)-2-imidazolone

The title compound was prepared according to a procedure substantially identical to Example 2.
Yield: 95%
M.P. 165–167° C.
$^1$H NMR (DMSO-$d_6$): 0.84(t,J=7.56 Hz,3H), 1.41–1.48(m, 2H), 3.03–3.33(m,4H), 3.92–4.02(m,2H), 6.95(s,1H), 7.26–7.98(m,9H), 11.18(s,1H)

EXAMPLE 5

Synthesis of 4-phenyl-1-(N-propylcarbamoyl-2-methylindoline-5-sulfonyl)-2-imidazolone The title compound was prepared according to a procedure substantially identical to Example 2.
Yield 95%
M.P.: 137.8–138.2° C.
$^1$H NMR (DMSO-$d_6$): 0.84(t,J=7.32 Hz,3H), 1.15(d,J=5.88 Hz,3H), 1.45–1.51(m,2H), 2.71–2.75(m,1H), 3.0–3.38(m, 2H), 4.58–4.61(m,1H), 7.05 (s,1H), 7.26–7.98(m,9H), 11.2 (s,1H)

EXAMPLE 6

Synthesis of 4-phenyl-1-(N-isopropylcarbamoylindoline-5-sulfonyl)-2-imidazolone

The title compound was prepared according to a procedure substantially identical to Example 2.
Yield 93%
M.P.: 214–216.5° C.
$^1$H NMR (DMSO-$d_6$): 1.10–1.17(m,6H), 3.14–3.18(m,2H), 3.83–4.04(m,3H), 6.60(d,J=7.8 Hz,1H), 7.27–7.98(m,9H), 11.18(s,1H)

EXAMPLE 7

Synthesis of 4-phenyl-1-(N-isopropylcarbamoyl-2-methylindoline-5-sulfonyl)-2-imidazolone The title compound was prepared according to a procedure substantially identical to Example 2.
Yield: 93%
M.P.: 154.3–156.5° C.
$^1$H NMR (DMSO-$d_6$): 1.10–1.19(m,9H), 3.16–3.20(m,2H), 3.83–4.04(m,3H), 6.57(d,J=7.55 Hz,1H), 7.27–7.98(m,9H), 11.20(s,1H)

EXAMPLE 8

Synthesis of 4-phenyl-1-(N-t-butylcarbamoylindoline-5-sulfonyl)-2-imidazolone

The title compound was prepared according to a procedure substantially identical to Example 2.
Yield: 76%
M.P. 221.7–223° C.
$^1$H NMR (DMSO-$d_6$): 1.39(s,9H), 2.62–2.80(m,2H), 3.89–4.01(m,2H), 6.12 (s,1H), 7.24–7.99(m,9H), 11.25(s, 1H)

EXAMPLE 9

Synthesis of 4-phenyl-1-[N-(4-nitrobenzoyl)indoline-5-sulfonyl]-2-imidazolone

4-Phenyl-1-(indoline-5-sulfonyl)-2-imidazolone (300 mg, 0.88 mmol) prepared in Preparation 3 was suspended in 10 ml of dichloromethane. Then, pyridine (85 µl, 1.05 mmol) and 4-nitrobenzoyl chloride (163 mg, 0.88 mmol) were added thereto one after another. The resulting reaction mixture was stirred at room temperature under nitrogen atmosphere for 5 hours while the reaction being monitored by TLC. After the reaction was completed, the whole mixture was diluted with dichloromethane, washed with brine, dried over anhydrous magnesium sulfate, concentrated, and finally purified by silica gel column chromatography (eluent:dichloromethane/methanol=15/1, v/v) to afford 400 mg of the title compound as a yellow solid.
Yield: 92%
M.P.: 244.8–246.3° C.
$^1$H NMR (DMSO-$d_6$): 3.16–3.20(m,2H), 4.00–4.04(m,2H), 7.28–8.37(m,13H), 11.22(s,1H)

EXAMPLE 10

Synthesis of 4-phenyl-1-[N-(4-aminobenzoyl)indoline-5-sulfonyl]-2-imidazolone.HCl 4-Phenyl-1-[N-(4-nitrobenzoyl)indoline-5-sulfonyl]-2-imidazolone (100 mg, 0.2 mmol) prepared in Example 9 and 1.5 ml of 50% Raney-Ni were suspended in 20 ml of methanol. The reaction mixture was stirred at room temperature under hydrogen atmosphere (5 bar) for 4 hours. The reaction mixture was filtered through Celite and then the filtrate was concentrated. The residue thus obtained was crystallized from a solvent mixture of methanol and dichloromethane (1:40, v/v) to afford the title compound in a free base form, which was then reacted with 20%(w/w) HCl—CH$_3$OH to provide 92 mg of the title compound as a white solid HCl salt.
Yield: 92%
M.P.: 199–201° C.
$^1$H NMR (DMSO-d$_6$): 3.12–3.15(m,2H), 4.00–4.17(m,2H), 5.79–6.0(brs,2H), 6.57(d,J=8.32 Hz,2H), 7.27–7.86(m, 11H), 11.21(s,1H).

EXAMPLE 11

Synthesis of 4-phenyl-1-[N-(4-nitrobenzoyl)-2-methylindoline-5-sulfonyl]-2-imidazolone The title compound was prepared according to a procedure substantially identical to Example 9.
Yield: 88%
M.P.:168.5–171.8° C.
$^1$H NMR (DMSO-d$_6$): 1.04–1.16(m,3H), 2.77–2.81(m,1H), 3.49–3.53(m,1H), 4.554.65(m,1H), 7.28–8.58(m,13H), 11.25(s,1H)

EXAMPLE 12

Synthesis of 4-phenyl-1-[N-(4-aminobenzoyl)-2-methylindoline-5-sulfonyl]-2-imidazolone.HCl The title compound was prepared according to a procedure substantially identical to Example 10.
Yield: 68%
M.P. 189–190° C.
$^1$H NMR (DMSO-d$_6$): 1.06–1.21 (d,J=4.99 Hz,3H), 2.74–2.78(m,1H), 3.41–3.47(m,1H), 4.73–4.77(m,1H), 5.74–5.79(brs,1H), 6.56(d,J=8.53 Hz,2H), 7.27–7.84(m, 11H), 11.22(s,1H)

EXAMPLE 13

Synthesis of 4-phenyl-1-(N-benzoylindoline-5-sulfonyl)-2-imidazolone

The title compound was prepared according to a procedure substantially identical to Example 9.
Yield 96%
M.P.: 167.4–170° C.
$^1$H NMR (DMSO-d$_6$): 3.13–3.18(m,2H), 4.03–4.07(m,2H), 7.27–8.31(m,14H), 11.24(s,1H)

EXAMPLE 14

Synthesis of 4-phenyl-1-[N-(4-ethoxybenzoyl)indoline-5-sulfonyl]-2-imidazolone

The title compound was prepared according to a procedure substantially identical to Example 9.
Yield: 89%
M.P.: 249–252.8° C.
$^1$H NMR (DMSO-d$_6$): 1.33(t,J=6.84 Hz,3H), 3.13–3.17(m, 2H), 4.054.13(m,4H), 6.99–7.86(m,13H), 11.23(s,1H)

EXAMPLE 15

Synthesis of 4-phenyl-1-(N-nicotinylindoline-5-sulfonyl)-2-imidazolone

The title compound was prepared according to a procedure substantially identical to Example 9.
Yield 82%
M.P.: 244–245.2° C.
$^1$H NMR (DMSO-d$_6$): 3.15–3.19(m,2H), 4.06–4.10(m,2H), 7.28–9.06(m,13H), 11.24(s,1H)

EXAMPLE 16

Synthesis of 4-phenyl-1-(N-furanoylindoline-5-sulfonyl)-2-imidazolone

The title compound was prepared according to a procedure substantially identical to Example 9.
Yield: 85%
M.P. 255.5–257° C.
$^1$H NMR (DMSO-d$_6$): 3.26–3.28(m,2H), 4.47–4.51 (m,2H ), 6.73(s,1H), 7.29–8.24(m,11H ), 11.23(s,1H)

EXAMPLE 17

Synthesis of 4-phenyl-1-(N-thiophenoylindoline-5-sulfonyl)-2-imidazolone

The title compound was prepared according to a procedure substantially identical to Example 9.
Yield 97%
M.P.: 258.2–259.5° C.
$^1$H NMR (DMSO-d$_6$): 3.25–3.29(m,2H), 4.47–4.51(m,2H), 7.21–8.20(m,12H), 11.24(s,1H)

EXAMPLE 18

Synthesis of 4-phenyl-1-[N-(4-chlorobenzoyl)indoline-5-sulfonyl]-2-imidazolone

The title compound was prepared according to a procedure substantially identical to Example 9.
Yield: 87%
M.P. 220.3–221.3° C.
$^1$H NMR (DMSO-d$_6$): 3.13–3.18(m,2H), 4.00–4.07(m,2H), 7.27–7.87(m,13H), 11.24(s, 1H)

EXAMPLE 19

Synthesis of 4-phenyl-1-[N-(4-chloroacetylaminobenzoyl)indoline-5-sulfonyl]-2-imidazolone 4-Phenyl-1-[N-(4-aminobenzoyl)indoline-5-sulfonyl]-2-imidazolone (150 mg, 0.3 mmol) prepared in Example 10 was dissolved in 10 ml of dichloromethane. Pyridine (73 μl, 0.9 mmol) and chloroacetylchloride (36 μl, 0.45 mmol) were added thereto one after another, and then the reaction mixture was stirred at room temperature under nitrogen atmosphere for 2 hours. After stirring, the reaction mixture was diluted with 30 ml of dichloromethane, washed with water, dried over anhydrous magnesium sulfate, and then concentrated. The residue was purified by silica gel column chromatography (eluent:dichloromethane/methanol=10/1, v/v) to afford 130 mg of the title compound as a white solid.
Yield: 84%
M.P.: 188–189° C.
$^1$H NMR (DMSO-d$_6$): 3.14–3.18(m,2H), 4.08–4.12(m,2H), 4.29(s,2H), 7.27–7.86(m,13H), 10.58(s,1H), 11.24(s,1H)

EXAMPLE 20

Synthesis of 4-phenyl-1-[N-(4-chloroacetylaminobenzoyl)-2-methylindoline-5-sulfonyl]-2-imidazolone The title compound was prepared according to a procedure substantially identical to Example 19.

Yield: 72%
M.P.: 245.5–246.4° C.
$^1$H NMR (DMSO-$d_6$): 1.03(d,J=6.36 Hz,3H), 2.76–2.80(m, 1H), 3.45–3.51 (m,1H), 4.28(s,2H), 4.69–4.71(m,1H), 7.27–7.89(m,13H), 10.56(s,1H), 11.24 (s,1H)

EXAMPLE 21

Synthesis of 4-phenyl-1-(N-chloroacetyl-2-methylindoline-5-sulfonyl)-2-imidazolone 4-Phenyl-1-(2-methylindoline-5-sulfonyl)-2-imidazolone (300 mg, 0.85 mmol) prepared in Preparation 3 was dissolved in 10 ml of dichloromethane. Pyridine (75 μl, 0.93 mmol) and chloroacetylchloride (74 μl, 0.93 mmol) were added thereto one after another, and then the reaction mixture was stirred at room temperature under nitrogen atmosphere for 2 hours. After stirring, the reaction mixture was diluted with 50 ml of dichloromethane, washed with water, dried over anhydrous magnesium sulfate, and then concentrated. The residue was purified by silica gel column chromatography (eluent:dichloromethane/methanol=10/1, v/v) to afford 342 mg of the title compound as a white solid.
Yield: 94%
M.P.: 157–159° C.
$^1$H NMR (DMSO-$d_6$): 1.22(d,J=6.36 Hz,3H), 2.78–2.83(m, 1H), 3.42–3.44 (m,1H), 4.58–4.62(m,1H), 4.72–4.79(m, 1H), 7.27–8.56(m,9H), 11.25(s,1H)

EXAMPLE 22

Synthesis of 4-phenyl-1-(N-methylaminoacetyl-2-methylindoline-5-sulfonyl)-2-imidazolone.HCl 4-Phenyl-1-(N-chloroacetyl-2-methylindoline-5-sulfonyl)-2-imidazolone (120 mg, 0.278 mmol) prepared in Example 21 was dissolved in 10 ml of acetone, and then sodium iodide (63 mg, 0.42 mmol) was added thereto. The reaction mixture was stirred at room temperature for 2 hours and the solvent was evaporated. The residue was dissolved in 10 ml of tetrahydrofuran. After 40% methylamine (239 μl, 2.78 mmol) was added thereto, the reaction mixture was stirred at room temperature for 6 hours. The solvent was removed under reduced pressure, then the residue was dissolved in 50 ml of dichloromethane, washed with water, dried over anhydrous magnesium sulfate, and concentrated. The residue was purified by silica gel column chromatography (eluent:dichloromethane/methanol=15/1, v/v) to afford the title compound in a free base form, which was then reacted with 20%(w/w) HCl—CH$_3$OH to provide 88 mg of the title compound as a white solid HCl salt.
Yield: 65%
M.P.: 197–199° C.
$^1$H NMR (DMSO-$d_6$): 1.23–1.26(m,6H), 2.84–2.89(m,1H), 4.07–4.09(m,1H), 4.33–4.35(m,2H), 4.67–4.71(m,1H), 7.36–8.17(m,9H), 8.88(brs,1H), 11.26(s,1H)

EXAMPLE 23

Synthesis of 4-phenyl-1-(N-isopropylaminoacetyl-2-methylindoline-5-sulfonyl)-2-imidazolone.HCl The title compound was prepared according to a procedure substantially identical to Example 22.
Yield: 76%
M.P.: 202–203.6° C.
$^1$H NMR (DMSO-$d_6$): 1.16–1.28(m,9H), 2.84–2.89(m,1H), 4.08–4.11(m,2H), 4.37–4.39(m,2H), 4.79–4.81(m,1H), 7.28–8.17(m,9H), 8.91(brs,1H), 11.27(s,1H)

EXAMPLE 24

Synthesis of 4-phenyl-1-(N-isopropylaminoacetylindoline-5-sulfonyl)-2-imidazolone.HCl The title compound was prepared according to a procedure substantially identical to Example 22.
Yield: 81%
M.P. 205–206° C.
$^1$H NMR (DMSO-$d_6$): 1.25–1.26(m,6H), 4.17–4.21(m,4H), 7.29–8.23(m,9H), 9.00(brs,1H), 11.26(s,1H)

EXAMPLE 25

Synthesis of 4-phenyl-1-(N-isobutylaminoacetyl-2-methylindoline-5-sulfonyl)-2-imidazolone.HCl The title compound was prepared according to a procedure substantially identical to Example 22.
Yield 84%
M.P. 197–199° C.
$^1$H NMR (DMSO-$d_6$): 0.89–0.95(m,6H), 1.24(d,J=5.89 Hz,3H), 1.97–2.05 (m,2H), 2.84–2.88(m,3H), 4.15–4.17(m, 1H), 4.34–4.40(m,1H), 4.72–4.80(m,1H), 7.28–8.18(m,9H), 9.00(brs,2H), 11.27(s,1H)

EXAMPLE 26

Synthesis of 4-phenyl-1-(N-isobutylaminoacetylindoline-5-sulfonyl)-2-imidazolone.HCl The title compound was prepared according to a procedure substantially identical to Example 22.
Yield 77%
M.P. 225° C.
$^1$H NMR (DMSO-$d_6$): 0.94–0.96(m,6H), 2.02–2.03(m,1H), 2.77–2.79(m,2H), 3.32–3.34(m,2H), 4.00–4.17(m,4H), 7.29–8.23(m,9H), 9.10(brs,1H), 11.26(s,1H)

EXAMPLE 27

Synthesis of 4-phenyl-1-(N-t-butylaminoacetyl-2-methylindoline-5-sulfonyl)-2-imidazolone.HCl The title compound was prepared according to a procedure substantially identical to Example 22.
Yield 65%
M.P.: 227.2–230° C.
$^1$H NMR (DMSO-$d_6$): 1.31(s,9H), 3.26–3.31(m,2H), 4.11–4.13(m,2H), 4.25–4.29(m,2H), 7.28–8.22(m,9H), 8.94 (brs, 1H), 11.27(s,1H)

EXAMPLE 28

Synthesis of 4-phenyl-1-(N-allylaminoacetyl-2-methylindoline-5-sulfonyl)-2-imidazolone.HCl The title compound was prepared according to a procedure substantially identical to Example 22.
Yield 85%
M.P.: 220–222° C.
$^1$H NMR (DMSO-$d_6$): 1.23(d,J=6.36 Hz,3H), 2.82–2.86(m, 1H), 4.08–4.12 (m,1H), 4.31–4.35(m,1H), 4.71–4.74(m, 1H), 5.39–5.49(m,2H), 5.88–5.97(m,1H), 7.27–8.19(m,9H), 9.44(brs,2H), 11.29(s,1H)

EXAMPLE 29

Synthesis of 4-phenyl-1-(N-ethylcarbamoylindoline-5-sulfonyl)4,5-dihydro-2-imidazolone 4-Phenyl-1-(indoline-5-sulfonyl)-4,5-dihydro-2-imidazolone (0.25 g, 0.73 mmol) prepared in Preparation 5 was dissolved in 10 ml of toluene and then ethylisocyanate (0.1 ml, 1.09 mmol) was added thereto. The reaction mixture was stirred at 50–60° C. for 18 hours. After the solvent was evaporated, the residue was dissolved in 50 ml of dichloromethane, washed twice with water, dried over anhydrous magnesium sulfate, and then concentrated under reduced pressure. The crude product thus obtained was purified by silica gel column chromatography (eluent:dichloromethane/methanol=15/1, v/v) to afford 0.22 g of the title compound.
Yield 90%
M.P.: 127° C.
$^1$H NMR (DMSO-$d_6$): 1.07(t,3H,J=6.9 Hz), 6.92(s,1H,J=7.16 Hz), 3.19–3.31 (m,4H), 3.43–3.52(m,1H), 3.94(t,2H, J=8.7 Hz), 4.22(t, 1H,J=8.99 Hz), 4.76 (t,1H,J=7.79 Hz), 6.92(s,1H), 7.19–7.35(m,5H), 7.63–7,66(m,2H), 7.93–7.97 (m,1H), 8.15(s,1H)

EXAMPLE 30

Synthesis of 4-phenyl-1-(N-propylcarbamoylindoline-5-sulfonyl)-4,5-dihydro-2-imidazolone The title compound was prepared according to a procedure substantially identical to Example 29.
Yield: 92%
M.P.: 197–198.6° C.
$^1$H NMR (DMSO-$d_6$): 0.86(t,1H,J=4.62 Hz), 1.48(q,2H,J=4.4 Hz), 3.05–3.19 (m,4H), 3.43–3.45(m,1H), 3.96(t,2H,J=5.57 Hz), 4.22(t,1H,J=5.55 Hz), 4.74–4.78 (m,1H), 6.93(t, 1H,J=3.47 Hz), 7.20–7.37(m,5H), 7.63–7.65(m,2H), 7.94–7.96 (m,1H), 8.16(s,1H)

EXAMPLE 31

Synthesis of 4-phenyl-1-(N-isopropylcarbamoylindoline-5-sulfonyl)-4,5-dihydro-2-imidazolone The title compound was prepared according to a procedure substantially identical to Example 29.
Yield 89%
M.P.: 120–122° C.
$^1$H NMR (DMSO-$d_6$): 0.99–1.28(m,6H), 3.13–3.18(m,2H), 3.34–3.45(m,1H), 3.84–3.99(m,3H), 4.20–4.24(m,1H), 4.74–4.78(m,1H), 6.58(d,1H,J=4.72), 7.21–7.37(m,5H), 7.63–7.66(m,2H), 7.95(d,1H,J=5.2 Hz), 8.16(s,1H)

EXAMPLE 32

Synthesis of 4-phenyl-1-(N-allylcarbamoylindoline-5-sulfonyl)-4,5-dihydro-2-imidazolone The title compound was prepared according to a procedure substantially identical to Example 29.
Yield: 69%
M.P. 217.3–218.7° C.
$^1$H NMR (DMSO-$d_6$): 3.16(t,2H,J=8.62 Hz), 3.4–3.5(m, 1H), 3.69–3.82(m,2H), 3.69(t,2H,J=8.88 Hz), 4.26(t, 1H,J=9.1 Hz), 4.76(t, 1H,J=7.5 Hz), 5.03–5.21 (m,2H), 5.79–6.0 (m,11H), 7.1–7.42(m,5H), 7.68–7.73(m,2H), 7.88–8.02(m, 1H), 8.16(s,1H)

EXAMPLE 33

Synthesis of 4-phenyl-1-(N-cyclohexylcarbamoylindoline-5-sulfonyl)-4,5-dihydro-2-imidazolone The title compound was prepared according to a procedure substantially identical to Example 29.
Yield: 82%
M.P.: 272.9–274.8° C.
$^1$H NMR (DMSO-$d_6$): 1.15–1.95(m,1OH), 3.18(t,2H,J=8.8 Hz), 3.46(dd,1H, J=6.6, 7.7 Hz), 7.20–8.05(m,13H)

EXAMPLE 34

Synthesis of 4-phenyl-1-(N-phenylcarbamoylindoline-5-sulfonyl)-4,5-dihydro-2-imidazolone The title compound was prepared according to a procedure substantially identical to Example 29.
Yield 76%
M.P.: 246.7–248.5° C.
$^1$H NMR (DMSO-$d_6$): 3.15–3.60(m,3H), 4.10–4.40(m,3H), 4.80–4.90(m,2H), 7.00–8.30(m,13H)

EXAMPLE 35

Synthesis of 4-phenyl-1-[N-(4-aminophenyl) carbamoylindoline-5-sulfonyl)-4,5-dihydro-2-imidazolone The title compound was prepared according to a procedure substantially identical to Example 29.
Yield: 63%
M.P.: 158–160° C.
$^1$H NMR (DMSO-$d_6$): 3.15–3.44(m,2H), 3.45–3.48(m,1H), 4.12–4.26(m,3H), 4.75–4.79(m,1H), 4.87(brs,2H), 6.54(d, 2H,J=9.15 Hz), 7.10–7.37(m,7H), 7.66–7.70(m,2H), 7.95(d, 1H,J=5.85 Hz), 8.15(s,1H), 8.37(s,1H)

EXAMPLE 36

Synthesis of 4-phenyl-1-[N-(4-methoxyphenyl) carbamoylindoline-5-sulfonyl]-4,5-dihydro-2-imidazolone The title compound was prepared according to a procedure substantially identical to Example 29.
Yield 68%
M.P.: 267.7–269.6° C.
$^1$H NMR (DMSO-$d_6$): 3.20–3.68(m,3H), 3.75(s,3H), 4.77 (dd,1H,J=6.5, 7.1 Hz), 6.85(d,2H,J=8.9 Hz), 7.30–7.75(m, 7H), 7.73–7.75(m,2H), 8.08(s,1H)

EXAMPLE 37

Synthesis of 4-phenyl-1-N-(4-methylthiophenyl) carbamoylindoline-5-sulfonyl]-4,5-dihydro-2-imidazolone The title compound was prepared according to a procedure substantially identical to Example 29.
Yield: 88%

M.P.: 260.1–261.3° C.
¹H NMR (DMSO-$d_6$): 2.45(s,3H), 3.17–3.62(m,3H), 4.20–4.26(m,3H), 4.75(dd, 1H,J=6.2, 7.9 Hz), 7.16–8.11(m, 12H)

EXAMPLE 38

Synthesis of 4-phenyl-1-(N-methylthiocarbamoylindoline-5-sulfonyl)-4,5-dihydro-2-imidazolone The title compound was prepared according to a procedure substantially identical to Example 29.
Yield: 75%
M.P.: 217.4–219.2° C.
¹H NMR (DMSO-$d_6$): 2.98(d,3H,J=3.92 Hz), 3.15(t,2H,J=8.25 Hz), 3.44–3.48 (m,1H), 4.14–4.29(m,2H), 4.78(t,1H, J=6.53 Hz), 7.21–7.39(m,5H), 7.68–7.71 (m,1H), 8.19(s, 11H), 8.34–8.36(brs,1H), 8.77(d,1H,J=8.63 Hz)

EXAMPLE 39

Synthesis of 4-phenyl-1-(N-ethylthiocarbamoylindoline-5-sulfonyl)-4,5-dihydro-2-imidazolone The title compound was prepared according to a procedure substantially identical to Example 29.
Yield: 86%
M.P.: 223.1–224.5° C.
¹H NMR (DMSO-$d_6$): 1.67(t,3H,J=7.09 Hz), 3.08–3.22(m, 2H), 3.42–3.67(m,3H), 4.05–4.27(m,3H), 4.72–4.86(m,1H), 7.13–7.43(m,5H), 7.62–7.8(m,2H), 8.20 (s,1H), 8.38(t,1H, J=4.8 Hz), 8.64(d, 1H,J=8.29 Hz)

EXAMPLE 40

Synthesis of 4-phenyl-1-(N-propylthiocarbamoylindoline-5-sulfonyl)-4,5-dihydro-2-imidazolone The title compound was prepared according to a procedure substantially identical to Example 29.
Yield: 86%
M.P. 222.3–223.5° C.
¹H NMR (DMSO-$d_6$): 0.87(t,3H,J=4.12 Hz), 1.62(q,2H,J=4.57 Hz), 3.15(t,2H, J=5.2 Hz), 3.45–3.54(m,3H), 4.78(t, 1H,J=4.42 Hz), 7.21–7.36(m,5H), 7.68–7.71 (m,2H), 8.18 (s,1H), 8.37(t,1H,J=4.11 Hz), 8.63(d,1H,J=5.47 Hz)

EXAMPLE 41

Synthesis of 4-phenyl-1-(N-butylthiocarbamoylindoline-5-sulfonyl)-4 5-dihydro-2-imidazolone The title compound was prepared according to a procedure substantially identical to Example 29.
Yield 93%
M.P. 186.3–187.7° C.
¹H NMR (DMSO-$d_6$): 0.91(t,3H,J=7.27 Hz), 1.28–1.37(m, 2H), 1.56–1.62(m,2H), 3.13(t,2H,J=8.35 Hz), 3.39–3.61(m, 3H), 4.13–4.29(m,3H), 4.75(t,1H,J=7.48), 7.22(d,2H,J=6.17 Hz), 7.29–7.42(m,3H), 7.63–7.79(m,2H), 8.19(s,1H), 8.3–8.42 (brs,1H), 8.62(d,2H,J=6.17 Hz)

EXAMPLE 42

Synthesis of 4-phenyl-1-(N-phenylthiocarbamoylindoline-5-sulfonyl)-4,5-dihydro-2-imidazolone The title compound was prepared according to a procedure substantially identical to Example 29.
Yield 80%
M.P. 182–182.7° C.
¹H NMR (DMSO-$d_6$): 3.13–3.27(m,2H), 3.41–3.51(m,1H), 4.12–4.3(m,3H), 4.78(t,1H,J=7.66 Hz), 7.12–8.35(m,13H), 10.15(s,1H)

EXAMPLE 43

Synthesis of 4-phenyl-1-[N-(4-methoxyphenyl) thiocarbamoylindoline-5-sulfonyl]-4,5-dihydro-2-imidazolone The title compound was prepared according to a procedure substantially identical to Example 29.
Yield 89%
M.P. 181–183° C.
¹H NMR (DMSO-$d_6$): 3.18(t,2H,J=8.32 Hz), 3.43–3.61(m, 1H), 3.75(s,31H), 4.21–4.40(m,3H), 4.81 (t, 1H,J=7.45 Hz), 6.95(d,2H,J=8.93 Hz), 7.23–7.42(m,5H), 7.64–7.82(m,2H), 8.17(s,1H), 8.42(d,2H,J=8.67 Hz), 9.96(s,1H)

EXAMPLE 44

Synthesis of 4-phenyl-1-[N-(2-methoxyphenyl) carbamoylindoline-5-sulfonyl]-4,5-dihydro-2-imidazolone The title compound was prepared according to a procedure substantially identical to Example 29.
Yield 69%
M.P.: 201.9–203.8° C.
¹H NMR (DMSO-$d_6$): 3.20–3.58(m,3H), 3.88(s,3H), 4.25–4.35(m,3H), 4.74(dd, 1H, J=6.6, 7.7 Hz), 7.05–8.20 (m,13H)

EXAMPLE 45

Synthesis of 4-phenyl-1-[N-(4-methylphenyl) carbamoylindoline-5-sulfonyl]-4,5-dihydro-2-imidazolone The title compound was prepared according to a procedure substantially identical to Example 29.
Yield: 82%
M.P. 222.7–224.2° C.
¹H NMR (DMSO-$d_6$): 4.25–4.30(m,3H), 4.78–4.80(m,1H), 7.00–8.20(m,12H)

EXAMPLE 46

Synthesis of 4-phenyl-1-[N-(4-fluorophenyl) thiocarbamoylindoline-5-sulfonyl]-4,5-dihydro-2-imidazolone The title compound was prepared according to a procedure substantially identical to Example 29.
Yield 72%
M.P.: 190.5–192.5° C.
¹H NMR (DMSO-$d_6$): 3.15–3.22(m,2H), 3.46–3.52(m,1H), 4.23–4.38(m,3H), 4.79(t,1H,J=7.32 Hz), 7.16–7.44(m,7H), 7.69–7.86(m,2H), 8.19(s,1H), 8.32–8.48 (m,2H), 10.07(s, 1H)

EXAMPLE 47

Synthesis of 4-phenyl-1-(N-benzoylindoline-5-sulfonyl)-4,5-dihydro-2-imidazolone 4-Phenyl-1-(indoline-5-sulfonyl)-4,5-dihydro-2-imidazolone (0.20 g, 0.58 mmol) prepared in Preparation 5 was dissolved in 12 ml of dichloromethane. Pyridine (0.1 ml, 0.58 mmol) and benzoyl chloride (0.1 g, 0.58mmol) were added dropwise one after another at 0° C. under nitrogen atmosphere. The reaction mixture was stirred at 0° C. for 2 hours and further stirred at room temperature for 3 hours. The reaction mixture was diluted with 20 ml of dichloromethane, washed twice with 10 ml of water, dried over anhydrous magnesium sulfate, and then concentrated under reduced pressure. The residue was purified by silica gel column chromatography (eluent:ethylacetate/hexane=2/1, v/v) to afford the title compound.
Yield: 92%
M.P. 127° C.
$^1$H NMR (DMSO-$d_6$): 3.16(t,2H,J=8.18 Hz), 3.53–3.46(dd, 1H,J=9.3, 9.28 Hz), 4.08(t,2H,J=8.38 Hz), 4.27(t,1H,J=8.99 Hz), 4.79(t,1H,J=7.35 Hz), 7.25–7.22 (m,2H), 7.38–7.31 (m,3H), 7.53–7.50(m,3H), 7.63–7,60(m,2H), 7.79(s,2H), 8.21 (s,1H)

EXAMPLE 48

Synthesis of 4-phenyl-1-[N-(4-methylbenzoyl) indoline-5-sulfonyl]-4,5-dihydro-2-imidazolone The title compound was prepared according to a procedure substantially identical to Example 47.
Yield: 68%
M.P.: 125° C.
$^1$H NMR (DMSO-$d_6$): 2.50–2.47(m,3H), 3.15(t,2H,J=8.28 Hz), 3.53–3.47 (dd,1H,J=9.48, 9.26 Hz), 4.07(t,2H,J=8.45 Hz), 4.27(t,1H,J=9.00 Hz), 4.79(t,1H, J=7.43 Hz), 7.42–7.22 (m,10H), 7.79–7.75(m,2H)

EXAMPLE 49

Synthesis of 4-phenyl-1-[N-(2-hydroxybenzoyl) indoline-5-sulfonyl]-4,5-dihydro-2-imidazolone The title compound was prepared according to a procedure substantially identical to Example 47.
Yield 76%
M.P. 221° C.
$^1$H NMR (DMSO-$d_6$): 3.16–3.12(m,2H), 3.50–3.48(m,1H), 3.96(bs,2H), 4.28–4.24(t,1H,J=7.99 Hz), 4.80–4.76(t,1H,J=7.45 Hz), 6.95–6.88(m,2H), 7.76–7.21 (m,8H), 8.21(s,1H), 8.30(s,1H)

EXAMPLE 50

Synthesis of 4-phenyl-1-[N-(4-methoxybenzoyl) indoline-5-sulfonyl]-4,5-dihydro-2-imidazolone The title compound was prepared according to a procedure substantially identical to Example 47.
Yield: 69%
M.P.: 220–222° C.
$^1$H NMR (DMSO-$d_6$): 3.15(t,2H,J=8.29 Hz), 3.53–3.36(dd, 1H,J=9.28, 9.31 Hz), 4.14(t,2H,J=9.38 Hz), 4.27(t,1H,J= 8.97 Hz), 4.80(t,1H,J=7.54 Hz), 7.05–7.02(d, 2H,J=8.77 Hz), 7.40–7.22(m,5H), 7.63–7.69(d,2H,J=8.74 Hz), 7.83–7.73(m,5H)

EXAMPLE 51

Synthesis of 4-phenyl-1-[N-(3,4-dimethoxybenzoyl) indoline-5-sulfonyl]-4,5-dihydro-2-imidazolone The title compound was prepared according to a procedure substantially identical to Example 47.
Yield: 60%
M.P.: 178–179° C.
$^1$H NMR (DMSO-$d_6$): 3.15(t,2H,J=8.26 Hz), 3.52–3.46(m, 1H), 3.78(s,3H), 3.82 (s,3H), 4.14(t,2H,J=8.41 Hz), 4.27(t, 1H,J=9.0 Hz), 4.79(t,1H,J=7.42 Hz), 7.05(d, 1H,J=8.92 Hz), 7.25–7.22(m,4H), 7.37–7.31(m,3H), 7.82–7,74(m,3H)

EXAMPLE 52

Synthesis of 4-phenyl-1-[N-(4-ethoxybenzoyl) indoline-5-sulfonyl]-4,5-dihydro-2-imidazolone The title compound was prepared according to a procedure substantially identical to Example 47.
Yield 62%
M.P. 216.5–217.5° C.
$^1$H NMR (DMSO-$d_6$): 1.34(t,3H,J=6.94 Hz), 3.15(t,2H,J= 8.3 Hz), 3.5(m,1H), 4.17–4.06(m,4H), 4.27(t,1H,J=8.96 Hz), 4.79(t,1H,J=7.36 Hz), 7.37–7.00(m,7H), 7.84–7.58(m, 5H)

EXAMPLE 53

Synthesis of 4-phenyl-1-[N-(4-chlorobenzoyl) indoline-5-sulfonyl]-4,5-dihydro-2-imidazolone The title compound was prepared according to a procedure substantially identical to Example 47.
Yield: 78%
M.P.: 235.3° C.
$^1$H NMR (DMSO-$d_6$): 3.15(t,2H,J=8.47 Hz), 3.50(dd,1H,J= 9.31, 9.28 Hz), 4.08 (t,2H,J=8.38 Hz), 4.27(t, 1H,J=9.0 Hz), 4.79(t,1H,J=7.38 Hz), 7.25–7.22(m,2H), 7.37–7.31(m,3H), 7.68–7.56(m,4H), 7.80–7.77(m,2H), 7.91–8.05(bs,1H)

EXAMPLE 54

Synthesis of 4-phenyl-1-[N-(4-fluorobenzoyl) indoline-5-sulfonyl]-4,5-dihydro-2 -imidazolone The title compound was prepared according to a procedure substantially identical to Example 47.
Yield 67%
M.P. 134° C.
$^1$H NMR (DMSO-$d_6$): 3.15(t,2H,J=8.33 Hz), 3.53–3.46(dd, 1H,J=9.3, 9.28 Hz), 4.08(t,2H,J=8.38 Hz), 4.27(t,1H,J=8.99 Hz), 4.79(t,1H,J=7.35 Hz), 7.40–7.22(m, 8H), 7.79–7.68(m, 5H)

EXAMPLE 55

Synthesis of 4-phenyl-1-[N-(4-nitrobenzoyl) indoline-5-sulfonyl]-4,5-dihydro-2-imidazolone The title compound was prepared according to a procedure substantially identical to Example 47.
Yield 86%
M.P.: 145° C.
$^1$H NMR (DMSO-$d_6$): 3.18(t,2H,J=8.35 Hz), 3.54–3.47(dd, 1H,J=9.28, 9.3 Hz), 4.05–4.01 (m,2H), 4.28(t, 1H,J=9.04 Hz), 4.80(t,1H,J=7.37 Hz), 7.25–7.22(m,2H), 7.38–7.31(m, 3H), 7.92–7.82(m,5H), 8.30–8.33(d,2H,J=8.73 Hz)

EXAMPLE 56

Synthesis of 4-phenyl-1-[N-(4-cyanobenzoyl) indoline-5-sulfonyl]-4,5-dihydro-2-imidazolone The title compound was prepared according to a procedure substantially identical to Example 47.

Yield: 85%
M.P.: 241–243° C.
1H NMR (DMSO-$d_6$): 3.16(t,2H,J=8.34 Hz), 3.53–3.41(m, 1H), 4.03(t,2H, J=8.15 Hz), 4.27(t,11H,J=8.92 Hz), 4.79(t, 1H,J=7.05 Hz), 7.38–7.22(m,5H), 7.82–7.80(m,4H), 8.02–7.98(d,2H,J=7.99 Hz), 8.21(s,1H)

EXAMPLE 57

Synthesis of 4-phenyl-1-[N-(4-aminobenzoyl) indoline-5-sulfonyl]-4,5-dihydro-2-imidazolone.HCl 4-Phenyl-1-[N-(4-nitrobenzoyl)indoline-5-sulfonyl]-4,5-dihydro-2-imidazolone (100 mg, 0.2 mmol) prepared in Example 55 and 1.5 ml of 50% Raney-Ni were suspended in 20 ml of a solvent mixture containing methanol and dichloromethane(3/1, v/v). The reaction mixture was stirred at room temperature under hydrogen atmosphere (5 bar) for 4 hours. The reaction mixture was filtered through Celite and then the filtrate was concentrated under reduced pressure. The residue thus obtained was crystallized from a solvent mixture of methanol and dichloromethane (1:40, v/v) to afford the title compound in a free base form, which was then reacted with 5 ml of 5.7%(w/w) HCl—$CH_3OH$ to provide 90 mg of the title compound as a white solid HCl salt.
Yield: 88%
M.P.: 216–217° C.
$^1$H NMR (DMSO-$d_6$): 3.15(t,J=8.3 Hz,2H), 3.49(dd, J=9.3, 9.3 Hz,1H), 4.15(t, J=8.3 Hz,2H), 4.27(dd,J=9.0, 9.0 Hz,1H), 4.79(dd,J=7.8, 6.6 Hz,1H), 6.95–6.97 (m,2H), 7.20–7.40(m,5H), 7.52–7.54(m,2H), 7.73–7.83(m,3H), 8.2 (s,1H)

EXAMPLE 58

Synthesis of 4-phenyl-1-[N-(3-chlorobenzoyl) indoline-5-sulfonyl]-4,5-dihydro-2-imidazolone The title compound was prepared according to a procedure substantially identical to Example 47.
Yield: 72%
M.P.: 132–136° C.
$^1$H NMR (DMSO-$d_6$): 3.16(t,2H,J=8.38 Hz), 3.53–3.47(dd, 1H,J=9.39, 9.34 Hz), 4.06(t,2H,J=8.58 Hz), 4.27(t,2H,J= 9.00 Hz), 4.79(t,1H,J=7.35 Hz), 7.22–7.41 (m,5H), 7.80–7.53(m,6H), 9.01(bs,1H), 8.21(s,1H)

EXAMPLE 59

Synthesis of 4-phenyl-1-[N-(3,5-dichlorobenzoyl) indoline-5-sulfonyl]-4,5-dihydro-2-imidazolone The title compound was prepared according to a procedure substantially identical to Example 47.
Yield 79%
M.P.: 235.8–236° C.
$^1$H NMR (DMSO-$d_6$): 3.19(t,2H,J=8.32 Hz), 3.53–3.49(m, 1H), 4.06(t,2H, J=8.36 Hz), 4.28(t,1H,J=9.00 Hz), 4.81(t, 1H,J=8.34 Hz), 7.25–7.22(m,2H), 7.38–7.31(m,4H), 7.71–7.70(m,2H), 7.81–7.80(m,3H)

EXAMPLE 60

Synthesis of 4-phenyl-1-[N-(3-fluorobenzoyl) indoline-5-sulfonyl]-4,5-dihydro-2-imidazolone The title compound was prepared according to a procedure substantially identical to Example 47.
yielld: 81%
M.P.: 202.5° C.
$^1$H NMR (DMSO-$d_6$): 3.16(t,2H,J=8.36 Hz), 3.53–3.47(dd, 1H,J=9.39, 9.33 Hz), 4.07(t,2H,J=8.37 Hz), 4.28(t,1H,J= 8.97 Hz), 4.79(t,1H,J=7.32 Hz), 7.58–7.22 (m,9H), 7.81(m, 1H), 8.2–7.8(bs,1H), 8.21(s,1H)

EXAMPLE 61

Synthesis of 4-phenyl-1-[N-(2,4-difluorobenzoyl) indoline-5-sulfonyl]-4,5-dihydro- 2-imidazolone The title compound was prepared according to a procedure substantially identical to Example 47.
Yield 71%
M.P.: 128° C.
$^1$H NMR (DMSO-$d_6$): 3.18(t,2H,J=8.61 Hz), 3.53–3.47(dd, 1H,J=9.28, 9.29 Hz), 3.97–3.87(bs,2H), 4.28(t,2H,J=9.04 Hz), 4.80(t, 1H,J=7.42 Hz), 7.50–7.22(m,8H), 7.81–7.65(m, 3H), 8.22(s,1H)

EXAMPLE 62

Synthesis of 4-phenyl-1-[N-(3-trifluoromethylbenzoyl)indoline-5-sulfonyl]-4,5-dihydro-2-imidazolone The title compound was prepared according to a procedure substantially identical to Example 47.
Yield 83%
M.P.: 119.2–119.4° C.
$^1$H NMR (DMSO-$d_6$): 3.16(t,2H,J=8.24 Hz), 3.5–3.47(m, 1H), 4.07(t,2H,J=8.34 Hz), 4.28(t,1H,J=8.99 Hz), 4.79(t,1H, J=7.30 Hz), 7.38–7.22(m,6H), 7.82–7.73(m, 3H), 7.99–7.90 (m,3H)

EXAMPLE 63

Synthesis of 4-phenyl-1-[N-(3-trifluoromethoxybenzoyl)indoline-5-sulfonyl]-4,5-dihydro-2-imidazolone The title compound was prepared according to a procedure substantially identical to Example 47.
Yield: 65%
M.P.: 129–131° C.
$^1$H NMR (DMSO-$d_6$): 3.16(t,2H,J=8.31 Hz), 3.50(m,1H), 4.07(t,2H,J=8.36 Hz), 4.27(t,1H,J=8.98 Hz), 4.29(t,1H,J= 7.45 Hz), 7.40–7.21 (m,5H), 8.2–7.7(m,7H)

EXAMPLE 64

Synthesis of 4-phenyl-1-[N-(4-trifluoromethoxybenzoyl)indoline-5-sulfonyl]-4,5-dihydro-2-imidazolone The title compound was prepared according to a procedure substantially identical to Example 47.
Yield: 71%
M.P.: 180–181.5° C.
$^1$H NMR (DMSO-$d_6$): 3.15(t,2H,J=8.34 Hz), 3.50(m,1H), 4.07(t,2H,J=8.39 Hz), 4.27(t,1H,J=8.99 Hz), 4.79(t,1H,J= 7.39 Hz), 7.5–7.2(m,7H), 7.8–7.7(m,5H)

EXAMPLE 65

Synthesis of (S)-(+)-4-phenyl-1-[N-(4-aminobenzoyl)indoline-5-sulfonyl]-4,5-dihydro-2-imidazolone.HCl (S)-(+)-4-phenyl-1-(indoline-5-sulfonyl)-4,5-dihydro-2-imidazolone (0.72 g, 2.09 mmol) prepared in Preparation 8 was dissolved in 20 ml of dichloromethane. Then, pyridine (186 µl, 2.23 mmol) and 4-nitrobenzoyl chloride (413 mg, 2.23 mmol) were added thereto at 0° C. under nitrogen atmosphere one after another. The reaction mixture was stirred at 5° C. for 2 hours and further stirred at room temperature for 3 hours. Then, the reaction mixture was diluted with 20 ml of dichloromethane, washed with water, dried over anhydrous magnesium sulfate, concentrated and finally purified by silica gel column chromatography (eluent:ethylacetate/hexane=2/1, v/v) to afford 0.97 g (Yield: 93%) of (S)-(+)-4-phenyl-1-[N-(4-nitrobenzoyl)-indoline-5-sulfonyl]-4,5-dihydro-2-imidazolone.

(S)-(+)-4-phenyl-1-[N-(4-nitrobenzoyl)-indoline-5-sulfonyl]-4,5-dihydro-2-imidazolone (100 mg, 0.2 mmol) was dissolved in a solvent mixture of methanol and dichloromethane (3/1, v/v). Then, 50% Raney-Ni was added thereto and the whole reaction mixture was stirred at room temperature under hydrogen atmosphere (5 bar) for 4 hours. The reaction mixture was filtered through Celite and then the filtrate was concentrated under reduced pressure. The residue thus obtained was purified by recrystallization from a solvent mixture of methanol and diethylether (1/40, v/v) to afford the title compound in a free base form, which was then treated with 23%(w/w) HCl—CH$_3$OH to provide 82 mg of the title compound as a white solid HCl salt.

Yield: 87%
M.P. 216.0° C.
[α]$_D$+20.4° (C=0.98, MeOH)
$^1$H NMR (DMSO-d$_6$): 3.15(t,J=8.3 Hz,2H), 3.49(dd,J=9.3, 9.3 Hz,1H), 4.15(t, J=8.3 Hz,2H), 4.27(dd,J=9.0, 9.0 Hz,1H), 4.79(dd,J=7.8, 6.6 Hz,1H), 6.95–6.97 (m,2H), 7.20–7.40(m,5H), 7.52–7.54(m,2H), 7.73–7.83(m,3H), 8.2 (s,1H)

EXAMPLE 66

Synthesis of (S)-(+)-4-phenyl-1-[N-{4-(2-aminopropanoyl)aminobenzoyl}indoline-5-sulfonyl]-4,5-dihydro-2-imidazolone.HCl To a solution of 1,3-dicyclohexylcarboimide (483 mg, 2.15 mmol) and 1-hydroxybenzotriazolehydrate (291 mg, 2.15 mmol) in 10 ml of tetrahydrofuran were added N-(t-butoxycarbonyl)-1-alanine (352 mg, 1.86 mmol) and 4-dimethylaminopyridine (50 mg, 0.41 mmol) in order. The reaction mixture was stirred at room temperature for 5 min. Then,. (S)-(+)-4-phenyl-1-[N-(4-aminobenzoyl)-indoline-5-sulfonyl]-4,5-dihydro-2-imidazolone (200 mg, 0.41 mmol) prepared in Example 65 was added thereto and the whole mixture was stirred at room temperature for 24 hours. After stirring, the reaction mixture was filtered. The filtrate was diluted with ethylacetate, washed with brine, dried over anhydrous magnesium sulfate, and then concentrated. The crude product thus obtained was purified by silica gel column chromatography (eluent:ethylacetate/hexane=2/1, v/v) to provide 260 mg (Yield:96%) of (S)-(+)-4-phenyl-1-[N-{4-(2-t-butoxycarbonylaminopropanoyl)-aminobenzoyl}indoline-5-sulfonyl]-4,5-dihydro-2-imidazolone.

(S)-(+)-4-phenyl-1-[N-{4-(2-t-butoxycarbonylaminopropanoyl)aminobenzoyl}indoline-5-sulfonyl]-4,5-dihydro-2-imidazolone (140 mg, 0.22 mmol) and p-cresol (57 µl, 0.55 mmol) were dissolved in a solvent mixture of trifluoroacetic acid and water (5 ml:0.5 ml). The reaction mixture was stirred at room temperature for 3 hours, and then 10 ml of diethylether was added thereto. The precipitate thus formed was collected, dissolved in 20 ml of water, neutralized using triethylamine, and then extracted with ethylacetate. The extract was dried over anhydrous magnesium sulfate, concentrated, and purified by silica gel column chromatography (eluent:dichloromethane/methanol=10/1, v/v) to afford the title compound in a free base form, which was then treated with 5.7%(w/w) HCl—CH$_3$OH to provide 110 mg of the title compound as a white solid HCl salt.

Yield: 82%
M.P.: 247.4° C.
[α]$_D$=+34.5° (C=0.02, MeOH)
$^1$H NMR (DMSO-d$_6$): 1.47(d,J=6.84 Hz,3H), 3.13–3.17(m, 2H), 3.47–3.51(m, 1H), 4.10–4.24(m,2H), 4.24–4.29(m, 1H), 4.77–4.81(m,1H), 7.22–8.46(m,13H), 11.25(s,1H)

EXAMPLE 67

Synthesis of (S)-(+)-4-phenyl-1-[N-{4-(2-aminoacetyl)aminobenzoyl}indoline-5-sulfonyl]-4,5-dihydro-2-imidazolone.HCl The title compound was prepared according to a procedure substantially identical to Example 66 except that N-(t-butoxycarbonyl)-L-glycine was used instead of N-(t-butoxycarbonyl)-1-alanine.

Yield: 71%
M.P.: 263.3° C.
[α]$_D$+35.6° (C=1.26, MeOH)
$^1$H NMR (DMSO-d$_6$): 3.13–3.17(m,2H), 3.47–3.49(m,1H), 3.83(s,2H), 4.10–4.14(m,2H), 4.24–4.29(m,1H), 4.77–4.81 (m,1H), 7.22–8.31(m,13H), 11.03(s,1H)

EXAMPLE 68

Synthesis of (S)-(−)-4-phenyl-1-[N-{4-(2-amino-3-phenyl-propanoyl)aminobenzoyl}indoline-5-sulfonyl]-4,5-dihydro-2-imidazolone.HCl The title compound was prepared according to a procedure substantially identical to Example 66 except that N-(t-butoxycarbonyl)-L-phenylglycine was used instead of N-(t-butoxycarbonyl)-1-alanine.

Yield: 66%
M.P.: 202.5° C.
[α]$_D$=−9.1° (C=2.76, MeOH)
$^1$H NMR (DMSO-d$_6$): 3.09–3.24(m,4H), 3.47–3.51(m,1H), 4.09–4.14(m,2H), 4.25–4.29(m,2H), 4.77–4.81(m,1H), 7.22–8.47(m,18H), 11.07(s,1H)

Hereinafter, the anti-tumor activity of compound (I) according to the present invention was evaluated in vitro and in vivo. The evaluation procedure and results were described in the following Experiments 1 to 4.

Experiment 1
In vitro antitumor activity against human tumor cell lines

In vitro antitumor activity of the compounds according to the present invention was determined by MTT assay method against the following human tumor cell lines:

A549 (ATCC CCL 185): human lung carcinoma
K562 (ATCC CCL 243): human chronic myelogenous leukemia
SK-OV-3 (ATCC HTB 77): human ovarian adenocarcinoma KB (ATCC CCL 17): human epidermoid carcinoma Colo205 (ATCC CCL 222): human colon adenocarcinoma In this test, the known antineoplastic compounds, Doxorubicin and Sulofenur, were used as the comparative agents.

Each of the tumor cells was cultured in RPMI 1640 media containing 10% fetal bovine serum, 100 IU/ml penicillin and 100 μg/ml streptomycin, and then periodically subcultured once or twice per week in trypsin-EDTA solution containing 0.05% trypsin and 0.53mM EDTA.4Na. The human tumor cell line thus obtained (10,000cells/100 μl) was plated on 96-well microplate and then cultured for 24 hrs at 37° C. in a 5% $CO_2$ incubator. Test compound was dissolved in DMSO, sterilized with 0.22 μm PVDF filter, and then serially 5-fold diluted from 40 μg/ml to 0.00256μg/ml. 100 μl of the sample solution thus prepared and RPMI 1640 medium only (control group) were added to 96-well microplate containing the human tumor cell, respectively. The final concentration of the test compound was in the range from 20 μg/ml to 0.00128 μg/ml and the concentration of DMSO was below 0.5%. The cells were cultured for 48 hrs at 37° C. in a 5% $CO_2$ incubator. MTT(3-(4,5-Dimethylthiazole-2-yl)-e,5-diphenyltetrazoliumbromide) was dissolved in physiological saline in a concentration of 2 mg/ml and the resulting solution was filtered through 0.22 μm PTFE filter. 25 μl of MTT solution thus prepared was added to each well of 96-well microplate and incubated for additional 4 hrs at 37° C. in a 5% $CO_2$ incubator. Then, the content of microplate was centrifuged at 1000 rpm for 10 min, and supernatant was removed by flicking. The formazan formed from MTT by mitochondrial succinate dehydrogenase was dissolved in 100 μl of DMSO. The absorbance of each well was measured at 540nm by micro ELISA reader and the cytotoxicity was calculated by dividing the absorbance of test group by the absorbance of control group. After the calculated cytotoxicity (%) was plotted, the concentration of 50% tumor growth inhibition concentration ($IC_{50}$) was estimated by Linear-Regression method.

The test results are described in the following Tables 1 to 5.

TABLE 1

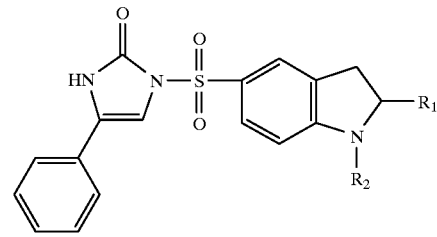

| Compound No. | $R_2$ | $R_1$ | $IC_{50}$ (μg/ml) A549 | KB | Colo205 | SK-OV-3 |
| --- | --- | --- | --- | --- | --- | --- |
| Doxonibicin | | | 0.742 | 0.914 | 0.973 | 2.255 |
| Sulofenur | | | 12.783 | | 48.9 | 78.2 |
| Example 1 | $CO_2Et$ | H | 0.374 | 0.017 | 0.906 | 10.050 |
| Example 2 | $CONHCH_2CH_3$ | H | 0.325 | 16.670 | — | 0.537 |
| Example 3 | $CONHCH_2CH_2$ | $CH_3$ | 0.111 | 0.006 | 0.265 | 0.509 |
| Example 4 | $CONH(CH_2)_2CH_3$ | H | 0.052 | — | <0.00128 | <0.00128 |
| Example 5 | $CONH(CH_2)_2CH_3$ | $CH_3$ | 0.090 | 0.105 | 0.519 | 0.146 |
| Example 6 | $CONHCH(CH_3)_2$ | H | <0.00128 | — | <0.00128 | <0.00128 |
| Example 7 | $CONHCH(CH_3)_2$ | $CH_3$ | 0.105 | 0.162 | 0.102 | 1.072 |
| Example 8 | $CONHC(CH_3)_3$ | H | 0.020 | 0.002 | 0.549 | 2.674 |
| Example 9 | $COC_6H_4(4-NO_2)$ | H | 0.528 | 0.045 | 0.651 | 0.106 |
| Example 10 | $COC_6H_4(4-NH_2)$ | H | 0.230 | 0.0001 | 0.334 | 0.529 |
| Example 11 | $COC_6H_4(4-NO_2)$ | $CH_3$ | 0.234 | 0.640 | 1.111 | 0.453 |
| Example 12 | $COC_6H_4(4-NH_2)$ | $CH_3$ | 0.321 | 0.072 | 0.861 | 0.509 |
| Example 13 | $COC_6H_5$ | H | 0.199 | 0.028 | 0.644 | 1.217 |
| Example 14 | $COC_6H_4(4-OEt)$ | H | 0.445 | 0.107 | 1.283 | 0.926 |
| Example 15 | Nicotinyl | H | 0.112 | 0.015 | 0.382 | 0.446 |
| Example 16 | Furanoyl | H | 0.065 | 0.011 | 0.460 | 2.074 |
| Example 17 | Thiophenoyl | H | 0.046 | 0.008 | 0.386 | 0.729 |

TABLE 2

[Chemical structure: phenyl-imidazolone-sulfonyl-indoline with R1 at 2-position and R2 on N]

| Compound No. | R₂ | R₁ | A549 | KB | Colo205 | IC$_{50}$ (μg/ml) SK-OV-3 |
|---|---|---|---|---|---|---|
| Example 18 | COC$_6$H$_4$(4-Cl) | H | 0.607 | 0.130 | 2.049 | >20 |
| Example 19 | COC$_6$H$_4$(4-NHCOCH$_2$Cl) | H | 0.438 | 0.046 | 0.580 | 0.202 |
| Example 20 | COC$_6$H$_4$(4-NHCOCH$_2$Cl) | CH$_3$ | 0.509 | 0.198 | 0.910 | 0.598 |
| Example 21 | COCH$_2$Cl | CH$_3$ | 1.128 | 1.531 | 0.834 | 4.709 |
| Example 22 | COCH$_2$NHCH$_3$ | CH$_3$ | 3.237 | 0.688 | 3.798 | 3.079 |
| Example 23 | COCH$_2$NHCH(CH$_3$)$_2$ | CH$_3$ | 1.139 | 0.429 | 3.450 | 4.030 |
| Example 24 | COCH$_2$NHCH(CH$_3$)$_2$ | H | 3.477 | 0.879 | 3.346 | 8.770 |
| Example 25 | COCH$_2$NHCH$_2$CH(CH$_3$)$_2$ | CH$_3$ | 3.231 | 0.246 | 3.072 | 1.398 |
| Example 26 | COCH$_2$NHCH$_2$CH(CH$_3$)$_2$ | H | 5.468 | 1.990 | 9.091 | 10.065 |
| Example 27 | COCH$_2$NHC(CH$_3$)$_3$ | CH$_3$ | 1.450 | 0.317 | 5.685 | 2.441 |
| Example 28 | COCH$_2$NHCH$_2$CH=CH$_2$ | CH$_3$ | 0.604 | 1.116 | 1.052 | 1.525 |

TABLE 3

[Chemical structure: phenyl-imidazolidinone-sulfonyl-indoline with R1 at 2-position and R2 on N]

| Compound No. | R₂ | R₁ | A549 | K562 | SK-OV-3 | IC$_{50}$ (μg/ml) Col205 |
|---|---|---|---|---|---|---|
| Doxorubicin | | | 0.670 | 0.276 | 1.315 | 6.30 |
| Sulofenur | | | 12.783 | 17.572 | 78.2 | 48.9 |
| Example 29 | CONHCH$_2$CH$_3$ | H | 0.318 | 1.001 | 1.95 | 1.001 |
| Example 30 | CONHCH$_2$CH$_2$CH$_3$ | H | 0.103 | 0.488 | 0.261 | 0.254 |
| Example 31 | CONHCH(CH$_3$)$_2$ | H | 0.073 | 0.439 | 0.280 | 0.258 |
| Example 32 | CONHCH$_2$CH=CH$_2$ | H | 0.042 | — | 0.685 | 7.100 |
| Example 33 | CONHC$_6$H$_{11}$ | H | 0.003 | 0.0037 | 0.043 | 0.172 |
| Example 34 | CONHC$_6$H$_5$ | H | 0.178 | <0.0064 | 0.16 | 1.259 |
| Example 35 | CONHC$_6$H$_4$(4-NH$_2$) | H | 0.286 | 0.004 | 0.763 | 3.240 |
| Example 36 | CONHC$_6$H$_4$(4-OCH$_3$) | H | 0.180 | 6.917 | 0.047 | 0.391 |
| Example 37 | CONHC$_6$H$_4$(4-SCH$_3$) | H | 2.340 | >20 | 0.716 | 0.710 |
| Example 38 | CSNHCH$_3$ | H | 0.092 | 0.00452 | 1.98 | 0.65 |
| Example 39 | CSNHCH$_2$CH$_3$ | H | 0.438 | 0.567 | 3.170 | 9.114 |
| Example 40 | CSNHCH$_2$CH$_2$CH$_3$ | H | 0.245 | 0.337 | 3.662 | — |
| Example 41 | CSNHCH$_2$CH$_2$CH$_2$CH$_3$ | H | 0.584 | 2.053 | 0.897 | 2.400 |
| Example 42 | CSNHC$_6$H$_5$ | H | 0.095 | 0.017 | 10.49 | 2.136 |
| Example 43 | CSNHC$_6$H$_4$(4-OCH$_3$) | H | 1.269 | 1.282 | 1.035 | — |
| Example 44 | CONHC$_6$H$_4$(2-OCH$_3$) | H | 0.135 | 0.290 | 0.273 | 1.465 |
| Example 45 | CONHC$_6$H$_4$(4-CH$_3$) | H | 0.311 | 1.032 | 0.813 | 3.265 |
| Example 46 | CSNHC$_6$H$_4$(4-F) | H | 3.292 | 3.941 | 3.130 | 8.736 |

TABLE 4

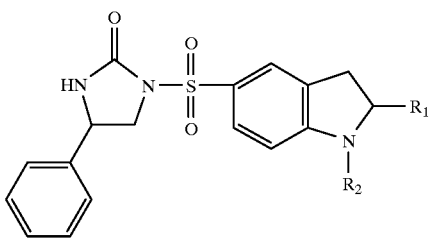

| Compound No. | $R_2$ | $R_1$ | A549 | c IC$_{50}$ ($\mu$g/ml) K562 | SK-OV-3 |
|---|---|---|---|---|---|
| Doxorubicin | | | 1.083 | 0.962 | 2.255 |
| Sulofenur | | | 12.78 | 17.57 | 78.2 |
| Example 47 | COC$_6$H$_5$ | H | 0.196 | 1.842 | 0.26 |
| Example 48 | COC$_6$H$_4$(4-CH$_3$) | H | 1.735 | 2.399 | >20 |
| Example 49 | COC$_6$H$_4$(2-OH) | H | 0.638 | 5.707 | 0.591 |
| Example 50 | COC$_6$H$_4$(4-OCH$_3$) | H | 1.564 | 2.186 | 1.369 |
| Example 51 | COC$_6$H$_4$(3,4-OCH$_3$) | H | 1.652 | 0.218 | 12.112 |
| Example 52 | COC$_6$H$_4$(4-OCH$_2$CH$_3$) | H | 0.101 | — | 2.219 |
| Example 53 | COC$_6$H$_4$(4-Cl) | H | 0.774 | 0.203 | 5.975 |
| Example 54 | COC$_6$H$_4$(4-F) | H | 0.590 | 3.643 | 2.328 |
| Example 55 | COC$_6$H$_4$(4-NO$_2$) | H | 1.699 | 8.876 | 2.088 |
| Example 56 | COC$_6$H$_4$(4-CN) | H | 1.590 | 4.965 | 0.968 |
| Example 57 | COC$_6$H$_4$(4-NH$_2$) | H | 0.090 | 0.203 | 0.572 |
| Example 58 | COC$_6$H$_4$(3-Cl) | H | 1.620 | 7.038 | 2.596 |
| Example 59 | COC$_6$H$_3$(3,5-Cl) | H | 2.024 | 1.882 | 16.531 |
| Example 60 | COC$_6$H$_4$(3-F) | H | 0.328 | 0.619 | 8.511 |
| Example 61 | COC$_6$H$_3$(2,4-F) | H | 1.937 | 5.664 | 1.520 |
| Example 62 | COC$_6$H$_4$(3-CF$_3$) | H | 2.184 | 1.368 | 11.774 |
| Example 63 | COC$_6$H$_4$(3-OCF$_3$) | H | 2.739 | — | 11.349 |
| Example 64 | COC$_6$H$_4$(4-OCF$_3$) | H | 0.695 | — | 2.957 |

TABLE 5

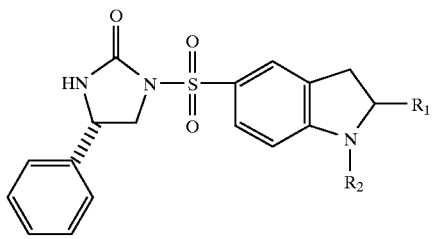

| Compound No. | $R_2$ | $R_1$ | A549 | Colo205 | K562 | IC$_{50}$ ($\mu$g/ml) SK-OV-3 |
|---|---|---|---|---|---|---|
| Doxorubicin | | | 1.68 | 0.961 | 0.780 | 1.60 |
| Sulofenur | | | 12.783 | 48.9 | 17.572 | 78.2 |
| Example 65 | COC$_6$H$_4$(4-NH$_2$) | H | 0.105 | 0.268 | 0.829 | 0.062 |
| Example 66 | COC$_6$H$_4$(4-NHCOCH(CH$_3$)NH$_2$) | H | 0.112 | 0.770 | 3.567 | 0.259 |
| Example 67 | COC$_6$H$_4$(4-NHCOCH$_2$NH$_2$) | H | 0.254 | 0.971 | 1.324 | 0.855 |
| Example 68 | COC$_6$H$_4$(4-NHCOCH(CH$_2$C$_6$H$_5$)NH$_2$) | H | 0.083 | 0.598 | 0.561 | 0.137 |

Experiment 2
In vivo antitumor activity against P388 murine leukemia cell

P388 murine leukemia cells were injected into BDF1 mouse intraperitoneally and grown in the peritoneal cavity. The P388 cells were periodically exudated and reinjected intraperitoneally into mouse for subculture.

The cells were exudated, washed, resuspended in saline ($2\times10^7$ cells/ml), and then injected intraperitoneally again into BDF1 mouse ($2\times10^6$ cells/0.1 ml).

Test compound dissolved in appropriate vehicle was administered intraperitonealy or orally into the mouse which was implanted with P388 murine leukemia tumor cells in the frequency of once per 2 days for 10 days. The vehicle was administered into the mouse of control group. Then, the number of live animals were daily checked to estimate the median survival time (MST).

T/C ratio(%) of each test compound was calculated according to the following formula, and the test results are shown in Table 6.

T/C(%)=(MST of test group÷MST of control group)×100

TABLE 6

| Compound No. | Dose (mg/kg) | Route | T/C rate (%) |
|---|---|---|---|
| Example 12 | 65 | p.o. | 115.4 |
| Example 29 | 6.25 | i.p. | 113.6 |
| Example 34 | 6.25 | i.p. | 140.9 |
| Example 57 | 100 | i.p. | 166.7 |
| Example 57 | 100 | p.o. | 175.0 |
| Example 57 | 65 | p.o. | 146.0 |
| Example 57 | 50 | p.o. | 133.3 |
| Example 65 | 65 | p.o. | 138.5 |

Experiment 3
In vivo antitumor activity against Colon 26 murine colon cancer cell Colon 26 murine cancer cells were injected into Balb/C mouse intradermally and grown in mouse abdominal skin to a solid tumor. The Colon 26 tumors were periodically excised from the mouse, digested with an enzyme mixture containing collagenase and DNase, and then intradermally reinjected into mouse for subculture.

The cells were washed, resuspended in saline ($5\times10^6$ cells/ml) and inoculated ($5\times10^5$ cells/0.1 ml) intradermally to abdominal part of Balb/C mouse of which hair was removed in advance. Each test compound was dissolved in a solvent mixture of 60% propylene glycol(PG), 40% cremophor RH60(CP), and distilled water(DW) in the volume ratio of 30:20:50. When the size of tumor reached at appropriate level, the test compound was administered orally into the mouse which was implanted with colon 26 tumor cells in the frequency of once per 2 days for 10 days. The vehicle was also administered into the mouse of control group. The major and minor axis of tumor in each group were regularly measured by vernier calipers to estimate the increase of the tumor volume. Tumor volume was calculated on the basis of the following formula Tumor volume(mm$^3$)=($\frac{1}{2}$)×[length of major axis(mm)]×[length of minor axis(mm)]$^{-2}$ When the tumor volume of the control group reached at about 1500 mm$^3$, the test animals were sacrificed by cervical dislocation and tumor was carefully excised and weighed. The inhibition rate of tumor growth (%) of each test compound was calculated as follows:

The inhibition rate of tumor growth(%)=100×[1−(Tumor weight of test group÷Tumor weight of control group)]

The results are shown in the following Table 7.

TABLE 7

| Compound No. | Dose (mg/kg) | Route | Inhibition rate of tumor growth (%) |
|---|---|---|---|
| Example 57 | 65 | p.o. | 67.4 |
| Example 65 | 65 | p.o. | 69.2 |
| Example 68 | 65 | p.o. | 45.3 |

Experiment 4
Acute toxicity test (LD$_{50}$)

Male Wistar Rat (Charles River Japan, ca, 6 weeks old) was used as test animal and sodium-carboxymethylcellulose (Na-CMC, Sigma Chemical, U.S.A.) was used as a vehicle control. Compounds 57 and 65 were suspended in 0.5% Na-CMC, respectively, before dosing. Test compounds were administered by gastric lavage with the dosage of 400, 550, 700, 850 and $^{1000}$ mg/kg. Control group was treated only with 0.5% Na-CMC. Each group was consisted of 5 rats. LD$_{50}$ value and 95% confidence intervals of each test compound were calculated according to probit method and the results thus obtained are described in the following Table 8 (95% confidence intervals are represented in the parenthesis).

TABLE 8

| Compound No. | Doses (mg/kg) | | | | | | |
|---|---|---|---|---|---|---|---|
| | 0 | 400 | 550 | 700 | 850 | 1000 | LD$_{50}$ |
| Example 27 | 0/5 | 0/5 | 1/5 | 3/5 | 5/5 | 5/5 | 644.3 (521.8–756.5) |
| Example 48 | 0/5 | 0/5 | 1/5 | 4/5 | 4/5 | 5/5 | 644.6 (506.8–756.6) |

As can be seen from the results of Table 8, the compound (I) according to the present invention has little acute toxicity against mammals including human being, therefore can be safely used as an antitumor agent.

Although this invention has been described in its preferred form with a certain degree of particularity, it is appreciated by those skilled in the art that the present disclosure of the preferred form has been made only by way of example and that numerous changes in the details of the construction, combination and arrangement of parts may be resorted to without departing from the spirit and scope of the invention.

What is claimed is:
1. An intermediate represented by the following formula (III):

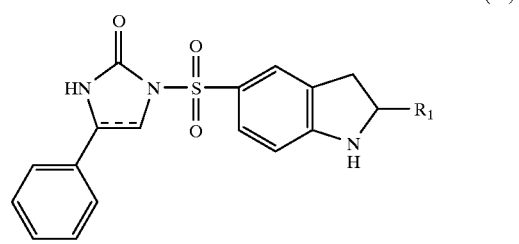

(III)

in which R$_1$ is hydrogen or methyl.

2. A process for preparing an intermediate of the following formula

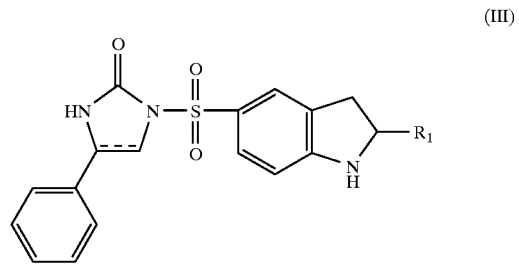

(III)

in which R$_1$ is hydrogen or methyl, wherein d) a compound represented by the following formula (VIIa):

(VIIa)

is reacted with a compound represented by the following formula (VIII):

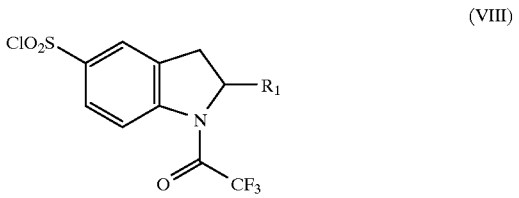

(VIII)

to provide a compound represented by the following formula (IXa):

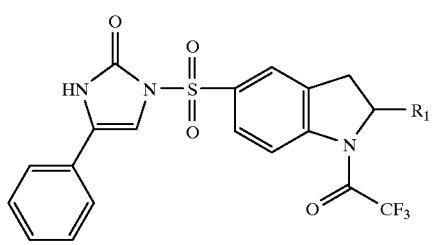

(IXa)

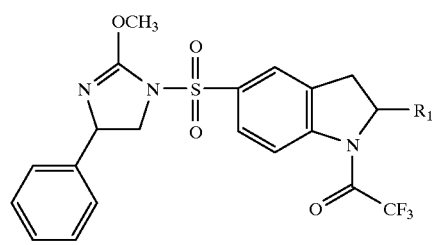

(IXb)

then the trifluoroacetyl group as an amino-protecting group of the compound of formula (IXa) is removed to prepare the compound represented by the following formula (IIIa):

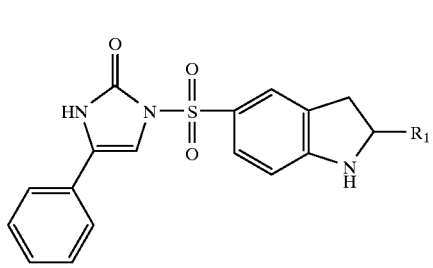

(IIIa)

in the above formulas R₁ is hydrogen or methyl; or e) a compound represented by the following formula (VIIb):

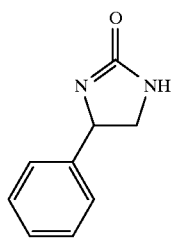

(VIIb)

is reacted with a compound represented by the following formula (VIII):

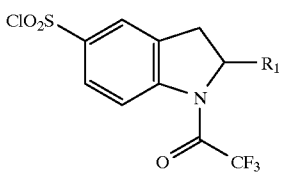

(VIII)

to provide a compound represented by the following formula (Ixb):

then the trifluoroacetyl group of the compound of formula (IXb) is removed and the product thus obtained is acid-hydrolyzed to prepare the compound represented by the following formula (IIIb):

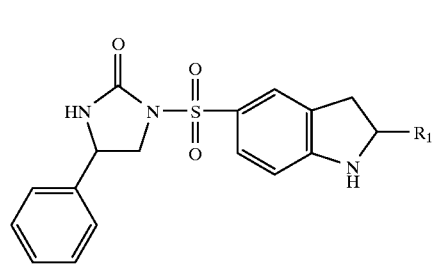

(IIIb)

in the above formulas, $R^1$ is hydrogen or methyl; or f) (S)-phenylglycinol represented by the following formula (X):

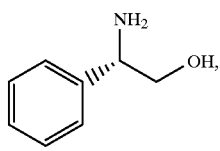

(X)

is reacted with phenylchloroformate (ClCOOPh) to provide a compound represented by the following formula (XI):

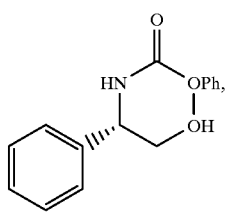

(XI)

which is reacted with methanesulfonylchloride ($CH_3SO_2Cl$) to produce a compound represented by the following formula (XII):

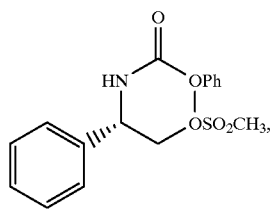
(XII)
then the compound of formula (XII) thus obtained is combined with a compound represented by the following formula (XIII):
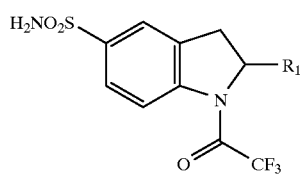
(XIII)
and deprotected to provide a compound represented by the following formula (IIIc):
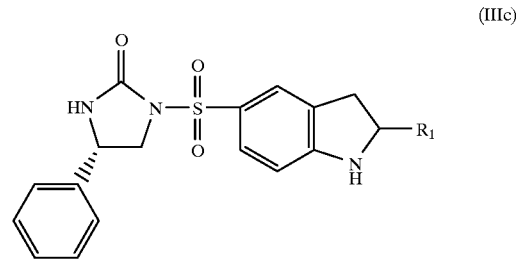
(IIIc)
in the above formulas, $R_1$ is hydrogen or methyl.
* * * * *